(12) United States Patent
Cooper et al.

(10) Patent No.: US 6,770,081 B1
(45) Date of Patent: *Aug. 3, 2004

(54) IN VIVO ACCESSORIES FOR MINIMALLY INVASIVE ROBOTIC SURGERY AND METHODS

(75) Inventors: Thomas G. Cooper, Menlo Park, CA (US); Christopher A. Julian, Los Gatos, CA (US); Michael Ikeda, San Jose, CA (US); Daniel T. Wallace, Redwood City, CA (US); David J. Rosa, San Jose, CA (US); Andris D. Ramans, Mountain View, CA (US); Frederic H. Moll, Woodside, CA (US); Robert G. Younge, Portola Valley, CA (US)

(73) Assignee: Intuitive Surgical, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/478,953

(22) Filed: Jan. 7, 2000

(51) Int. Cl.⁷ .............................................. A61B 19/00
(52) U.S. Cl. ...................................................... 606/130
(58) Field of Search ........................ 606/130; 128/898; 600/102, 114, 227, 228, 229

(56) References Cited

U.S. PATENT DOCUMENTS

| | | | | |
|---|---|---|---|---|
| 4,899,730 A | | 2/1990 | Stennert et al. | |
| 5,217,003 A | * | 6/1993 | Wilk | 128/4 |
| 5,226,429 A | * | 7/1993 | Kuzmak | 128/898 |
| 5,634,937 A | * | 6/1997 | Mollenauer et al. | 606/213 |
| 5,762,458 A | * | 6/1998 | Wang et al. | 414/1 |
| 5,792,135 A | | 8/1998 | Madhani et al. | |
| 5,797,835 A | * | 8/1998 | Green | 600/106 |
| 5,797,900 A | | 8/1998 | Madhani et al. | |
| 5,808,665 A | * | 9/1998 | Green | 348/65 |
| 5,971,976 A | * | 10/1999 | Wang et al. | 606/1 |
| 6,309,397 B1 | * | 10/2001 | Julian et al. | 606/130 |
| 6,325,808 B1 | * | 12/2001 | Bernard et al. | 606/139 |
| 6,409,735 B1 | * | 6/2002 | Andre et al. | 606/130 |

\* cited by examiner

*Primary Examiner*—Eduardo C. Robert
(74) *Attorney, Agent, or Firm*—Townsend and Townsend and Crew LLP

(57) ABSTRACT

Surgical accessories are presented in vivo and used by surgical tools in the surgical site to perform additional tasks without the need to remove the tools from the surgical site for tool change or instrument loading. Some accessories need to be actuated to effect a predetermined treatment, such as an aortic punch, clamps, pliers, and the like. For such accessories, the actuation can conveniently be performed by an operator such as an assistant remotely from outside the patient's body while placement of the accessories takes place in the surgical site by manipulating the accessories using robotic surgical tools in the site. A lockdown feature may be incorporated in accessories to lock them in place remotely from outside the surgical site upon actuation.

42 Claims, 20 Drawing Sheets

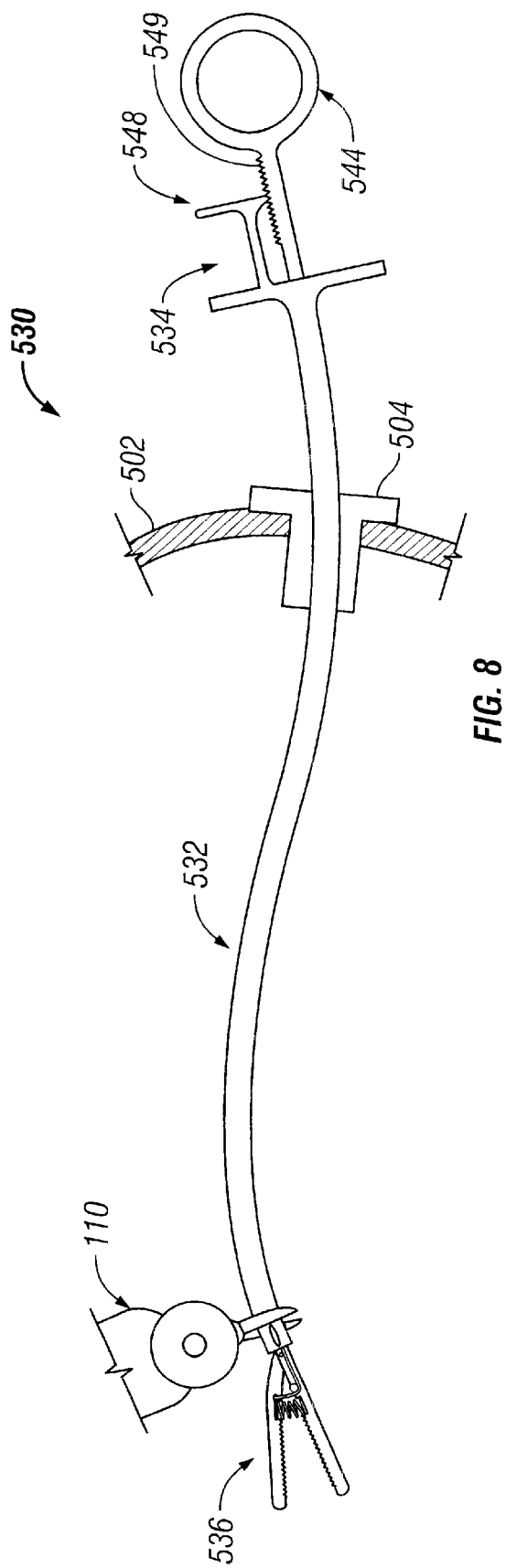
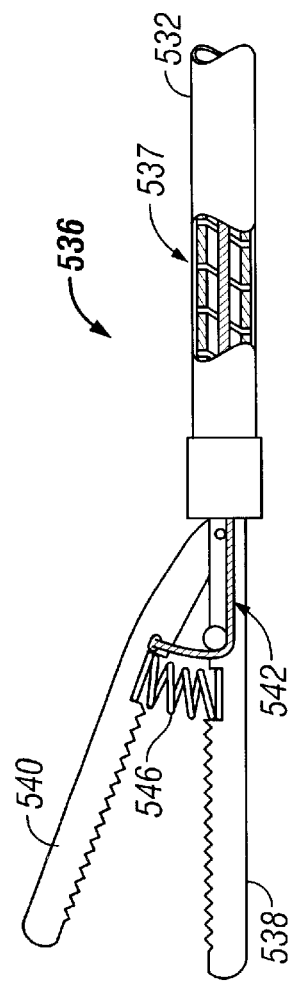
FIG. 8
FIG. 8A

IN VIVO ACCESSORIES FOR MINIMALLY INVASIVE ROBOTIC SURGERY AND METHODS

CROSS-REFERENCES TO RELATED APPLICATIONS

This application is a continuation-in-part of and claims priority from U.S. patent application Ser. No. 09/453,978 (now U.S. Pat. No. 6,309,379), entitled "In Vivo Accessories for Minimally Invasive Robotic Surgery", filed on Dec. 2, 1999. This application is related to U.S. application Ser. No. 09/464,455 entitled "Devices and Methods for Presenting and Regulating Auxiliary Information on an Image Display of a Telesurgical System to Assist an Operator in Performing a Surgical Procedure", filed Dec. 14, 1999; and U.S. patent application Ser. No. 09/436,524, entitled "Stabilizer for Robotic Beating Heart Surgery", filed on Nov. 9, 1999. The entire disclosures of these applications are incorporated herein by reference.

This application is related to the following patents and patent applications, the full disclosures of which are incorporated herein by reference: PCT International application No. PCT/US98/19508, entitled "Robotic Apparatus", filed on Sep. 18, 1998; U.S. application Ser. No. 09/418,726, entitled "Surgical Robotic Tools, Data Architecture, and Use", filed on Oct. 15, 1999; U.S. application Ser. No. 09/457,406, entitled "Image Shifting for a Telerobotic System", filed on Dec. 7, 1999; U.S. application Ser. No. 09/378,173, entitled "Stereo Imaging System for Use in Telerobotic System", filed on Aug. 20, 1999; U.S. application Ser. No. 09/398,507, entitled "Master Having Redundant Degrees of Freedom", filed on Sep. 17, 1999; U.S. application Ser. No. 09/399,457, entitled "Cooperative Minimally Invasive Telesurgery System", filed on Sep. 17, 1999; U.S. application Ser. No. 09/373,678, entitled "Camera Referenced Control in a Minimally Invasive Surgical Apparatus", filed on Aug. 13, 1999; U.S. application Ser. No. 09/398,958, entitled "Surgical Tools for Use in Minimally Invasive Telesurgical applications", filed on Sep. 17, 1999; and U.S. Pat. No. 5,808,665, entitled "Endoscopic Surgical Instrument and Method for Use", issued on Sep. 15, 1998.

BACKGROUND OF THE INVENTION

Advances in minimally invasive surgical technology could dramatically increase the number of surgeries performed in a minimally invasive manner. Minimally invasive medical techniques are aimed at reducing the amount of extraneous tissue that is damaged during diagnostic or surgical procedures, thereby reducing patient recovery time, discomfort, and deleterious side effects. The average length of a hospital stay for a standard surgery may also be shortened significantly using minimally invasive surgical techniques. Thus, an increased adoption of minimally invasive techniques could save millions of hospital days, and millions of dollars annually in hospital residency costs alone. Patient recovery times, patient discomfort, surgical side effects, and time away from work may also be reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments. The laparoscopic surgical instruments generally include a laparoscope (for viewing the surgical field) and working tools. The working tools are similar to those used in conventional (open) surgery, except that the working end or end effector of each tool is separated from its handle by an extension tube. As used herein, the term "end effector" means the actual working part of the surgical instrument and can include clamps, graspers, scissors, staplers, and needle holders, for example. To perform surgical procedures, the surgeon passes these working tools or instruments through the cannula sleeves to an internal surgical site and manipulates them from outside the abdomen. The surgeon monitors the procedure by means of a monitor that displays an image of the surgical site taken from the laparoscope. Similar endoscopic techniques are employed in, e.g., arthroscopy, retroperitoneoscopy, pelviscopy, nephroscopy, cystoscopy, cisternoscopy, sinoscopy, hysteroscopy, urethroscopy and the like.

There are many disadvantages relating to current minimally invasive surgical (MIS) technology. For example, existing MIS instruments deny the surgeon the flexibility of tool placement found in open surgery. Most current laparoscopic tools have rigid shafts, so that it can be difficult to approach the worksite through the small incision. Additionally, the length and construction of many endoscopic instruments reduces the surgeon's ability to feel forces exerted by tissues and organs on the end effector of the associated tool. The lack of dexterity and sensitivity of endoscopic tools is a major impediment to the expansion of minimally invasive surgery.

Minimally invasive telesurgical robotic systems are being developed to increase a surgeon's dexterity when working within an internal surgical site, as well as to allow a surgeon to operate on a patient from a remote location. In a telesurgery system, the surgeon is often provided with an image of the surgical site at a computer workstation. While viewing a three-dimensional image of the surgical site on a suitable viewer or display, the surgeon performs the surgical procedures on the patient by manipulating master input or control devices of the workstation. The master controls the motion of a servomechanically operated surgical instrument. During the surgical procedure, the telesurgical system can provide mechanical actuation and control of a variety of surgical instruments or tools having end effectors such as, e.g., tissue graspers, needle drivers, or the like, that perform various functions for the surgeon, e.g., holding or driving a needle, grasping a blood vessel, or dissecting tissue, or the like, in response to manipulation of the master control devices.

A typical surgery employs a number of different surgical instruments. When a different tool is desired during the surgical procedure, the surgical instrument is typically withdrawn from the surgical site so that it can be removed from its associated arm and replaced with an instrument bearing the desired end effector. The desired surgical instrument is then inserted into the surgical site.

A surgical instrument may also be withdrawn from a surgical site for reasons other than to replace the end effector. For example, the loading of a clip in a clip applier used in affixing tissue typically occurs outside of the patient's body. Each time a new clip is desired, the clip applier is removed from the surgical site to load the clip and then reintroduced into the patient's body to apply the clip. Tool exchange and instrument loading for a robotic system takes time. Providing additional surgical instruments in the surgical site (and the typically associated need to make additional incisions in the patient's body) may be an undesirable alternative for any number of reasons, e.g., due to space constraints, increase in system complexities, and/or cost.

SUMMARY OF THE INVENTION

The present invention is generally directed to robotic surgery methods, devices, and systems. The invention overcomes the problems and disadvantages of the prior art by providing surgical clips and/or other in vivo accessories at the surgical site. These in vivo accessories can be manipulated by robotic surgical tools in the site for performing different tasks. The accessories can be held by a dedicated accessory holder or support that is introduced into the surgical site through a separate opening. Alternatively, the accessories can be supported on the body of one of the surgical tools, and can be manipulated using another surgical tool in the surgical site. The surgical tools in the surgical site can use the accessories for performing a wide range of additional tasks without leaving the surgical site. In this way, the need to exchange tools and load instruments outside the surgical site is reduced, thereby minimizing "down time".

Some "active" accessories need to be actuated to effect a predetermined treatment, such as an aortic punch, clamps, pliers, and the like. For such accessories, the actuation can conveniently be performed by an operator such as an assistant remotely from outside the patient's body while placement of the accessories takes place in the surgical site by manipulating the accessories using robotic surgical tools in the site. A lockdown feature may be incorporated in accessories to lock them in place remotely from outside the surgical site upon actuation. An example involves locking clamp accessories in a closed position for clamping an aorta. After activating the lockdown feature, the assistant is freed to move on to the next task. In addition, the robotic surgical tool used to position the accessory may be removed after activation of the lockdown so that it is available to perform the next task. In this way, the robotic surgical tool inside the surgical site need only be used for a brief period of time to position the accessory and hold it in place until actuation and lockdown is performed remotely from the outside. This approach makes efficient use of the tools inside the surgical site and operator time.

In accordance with an aspect of the present invention, a method of performing minimally invasive robotic surgery in a body cavity of a patient includes introducing at least one surgical accessory and a robotic surgical tool into the cavity. The surgical accessory is coupled with the robotic surgical tool inside the cavity after separately introducing the surgical accessory and the robotic surgical tool into the cavity. The surgical accessory is actuated from outside the cavity of the patient to effect a predetermined treatment. The surgical accessory may be decoupled from the robotic surgical tool inside the cavity.

In some embodiments, the surgical accessory includes a movable member movable in the actuating step between a rest position and an actuated position. The movable member may be locked in the actuated position. In one embodiment, actuating the surgical accessory includes connecting the surgical accessory with a portion of the body cavity in the actuated position. Locking the movable member of the surgical accessory in the actuated position includes maintaining connection of the surgical accessory with the portion of the body cavity.

In another embodiment, two clamp accessories are introduced into the cavity. The clamp accessories are clenched around portions of an aorta with the clamp accessories in contact, desirably near the clamp tips, to enclose a region of the aorta, thereby partially occluding the aorta.

In accordance with another aspect of the invention, a method of performing minimally invasive robotic surgery in a body cavity of a patient comprises introducing at least one surgical accessory and a robotic surgical tool into the cavity. The surgical accessory is coupled with the robotic surgical tool inside the cavity after separately introducing the surgical accessory and the robotic surgical tool into the cavity. The robotic surgical tool is manipulated from outside the body cavity of the patient to position the surgical accessory within the body cavity. The surgical accessory is actuated from outside the body cavity of the patient to interact with a portion of the body cavity.

In accordance with another aspect of the invention, a robotic surgical system for effecting a predetermined treatment of a target tissue at an internal surgical site within a patient body comprises a surgical accessory adapted for effecting the treatment. An accessory introducer has a proximal end and a distal end with an opening therebetween. The distal end of the introducer is insertable into the patient body so that the opening defines a first minimally invasive aperture. The surgical accessory is coupled with the distal end of the introducer and passable through the opening to the internal surgical site. A robotic arm supports a surgical tool, and has an end effector suitable for insertion through a second minimally invasive aperture to the internal surgical site. The end effector is coupleable with the surgical accessory within the internal surgical site so that the robot arm can manipulate the surgical accessory to direct the surgical accessory to the target tissue. In specific embodiments, the accessory is actuatable from outside the internal surgical site to effect the treatment.

In some embodiments, the surgical accessory includes a proximal end disposed outside the internal surgical site, a distal end inside the internal surgical site, and a flexible body between the proximal end and the distal end. Examples of surgical accessories include an aortic punch, a pair of clamps, a heart stabilizer, a multi-fire clip applier, a pair of pliers, and a magnetic extractor.

In accordance with another aspect of the present invention, a robotic surgical system for effecting a predetermined treatment of a target tissue at an internal surgical site within a patient body comprises a surgical accessory adapted for effecting the treatment. The surgical accessory is configured for insertion through a first minimally invasive aperture to the internal surgical site. A robotic arm supports a surgical tool. The surgical tool has an end effector suitable for insertion through a second minimally invasive aperture to the internal surgical site. The end effector is coupleable with the surgical accessory within the internal surgical site so that the robot arm can manipulate the surgical accessory to direct the surgical accessory to the target tissue. An actuation member is configured to be inserted through a third minimally invasive aperture to the internal surgical site. The actuation member is coupleable with the surgical accessory within the internal surgical site for actuating the surgical accessory for effecting the treatment at the target tissue.

In specific embodiments, the actuation member includes a locking element for releasably locking the actuation member with the surgical accessory inside the internal surgical site. The locking element is manipulatable from outside the internal surgical site. The end effector is coupleable with the actuation member within the internal surgical site to manipulate the actuation member for coupling with the surgical accessory.

BRIEF DESCRIPTION OF THE DRAWINGS

FIGS. 6D and 6E depict a preferred embodiment of the master control device shown in FIGS. 6A–6C having a locking mechanism for locking the slave end effector into an actuated position;

FIG. 8 is a schematic view of a cross clamp as an in vivo accessory;

FIG. 8A is a cross-sectional view of the distal end of the cross clamp of FIG. 7;

DESCRIPTION OF THE SPECIFIC PREFERRED EMBODIMENTS

As used herein, "end effector" refers to the actual working part that is manipulatable for effecting a predetermined treatment of a target tissue. For instance, some end effectors have a single working member such as a scalpel, a blade, or an electrode. Other end effectors have a pair of working members such as forceps, graspers, scissors, or clip appliers, for example.

As used herein, the terms "surgical instrument", "instrument", "surgical tool", or "tool" refer to a member having a working end which carries one or more end effectors to be introduced into a surgical site in a cavity of a patient, and is actuatable from outside the cavity to manipulate the end effector(s) for effecting a desired treatment of a target tissue in the surgical site. The instrument or tool typically includes a shaft carrying the end effector(s) at a distal end, and is preferably servomechanically actuated by a telesurgical system for performing functions such as holding or driving a needle, grasping a blood vessel, and dissecting tissue.

As used herein, the terms "surgical accessory" and "accessory" refer to an assisting member that is introduced into the surgical site in the cavity of the patient to be used by an instrument or tool to perform a desired function in the surgical site.

I. Exemplary Telesurgical System

Figures 1A, 1B:
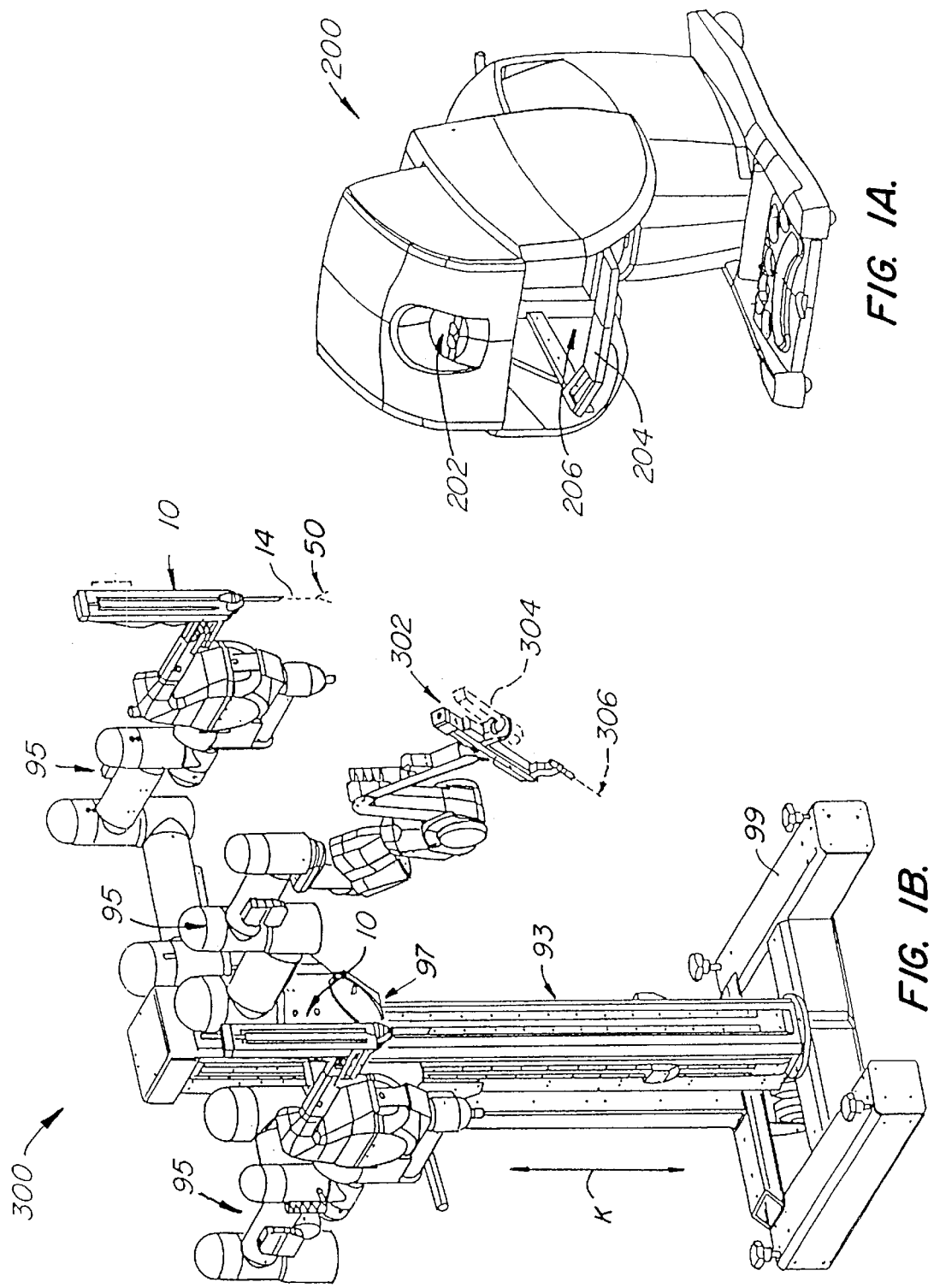
FIG. 1A is a perspective view of an operator station of a telesurgical system in accordance with an embodiment of the invention.
FIG. 1B is a perspective view of a cart or surgical station of the telesurgical system according to an embodiment of the invention, the cart of this particular embodiment carrying three robotically controlled arms, the movement of the arms being remotely controllable from the operator station shown in FIG. 1A.

FIG. 1A shows an operator station or surgeon's console 200 of a minimally invasive telesurgical system. The station 200 includes a viewer 202 where an image of a surgical site is displayed in use. A support 204 is provided on which an operator, typically a surgeon, can rest his or her forearms while gripping two master controls (not shown in FIG. 1A), one in each hand. The master controls are positioned in a space 206 inwardly beyond the support 204. When using the control station 200, the surgeon typically sits in a chair in front of the control station 200, positions his or her eyes in front of the viewer 202 and grips the master controls one in each hand while resting his or her forearms on the support 204.

FIG. 1B shows a cart or surgical station 300 of the telesurgical system. In use, the cart 300 is positioned close to a patient requiring surgery and is then normally caused to remain stationary until a surgical procedure to be performed has been completed. The cart 300 typically has wheels or castors to render it mobile. The station 200 is typically positioned remote from the cart 300 and can be separated from the cart 300 by a great distance, even miles away, but will typically be used within an operating room with the cart 300.

The cart 300 typically carries three robotic arm assemblies. One of the robotic arm assemblies, indicated by reference numeral 302, is arranged to hold an image capturing device 304, e.g., an endoscope, or the like. Each of the two other arm assemblies 10 respectively, includes a surgical instrument 14. The endoscope 304 has a viewing end 306 at a remote end of an elongate shaft thereof. It will be appreciated that the endoscope 304 has an elongate shaft to permit its viewing end 306 to be inserted through an entry port into an internal surgical site of a patient's body. The endoscope 304 is operatively connected to the viewer 202 to display an image captured at its viewing end 306 on the viewer 202. Each robotic arm assembly 10 is normally operatively connected to one of the master controls. Thus, the movement of the robotic arm assemblies 10 is controlled by manipulation of the master controls. The instruments 14 of the robotic arm assemblies 10 have end effectors that are mounted on wrist members which are pivotally mounted on distal ends of elongate shafts of the instruments 14, as is described in greater detail below. It will be appreciated that the instruments 14 have elongate shafts to permit the end effectors to be inserted through entry ports into the internal surgical site of a patient's body. Movement of the end effectors relative to the ends of the shafts of the instruments 14 is also controlled by the master controls.

The robotic arms 10, 10, 302 are mounted on a carriage 97 by means of manipulator positioning linkages ("setup joint arms") 95. The carriage 97 can be adjusted selectively to vary its height relative to a base 99 of the cart 300, as indicated by arrows K. The setup joint arms 95 are arranged to enable the lateral positions and orientations of the arms 10, 10, 302 to be varied relative to a vertically extending column 93 of the cart 300. Accordingly, the positions, orientations and heights of the arms 10, 10, 302 can be adjusted to facilitate passing the elongate shafts of the instruments 14 and the endoscope 304 through the entry ports to desired positions relative to the surgical site. When the surgical instruments 14 and endoscope 304 are so positioned, the setup joint arms 95 and carriage 97 are typically locked in position.

Figure 2A:
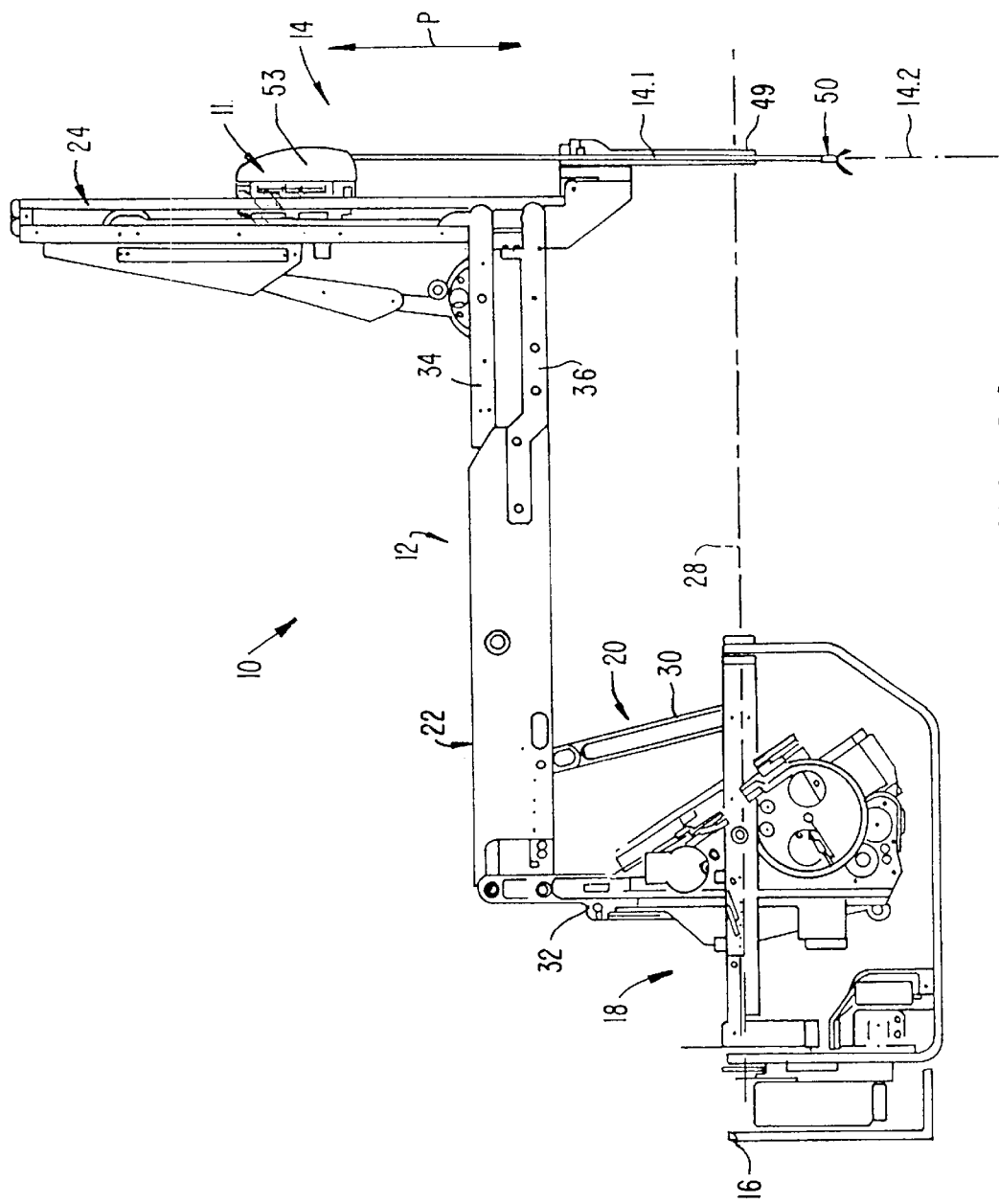
FIG. 2A is a side view of a robotic arm and surgical instrument assembly according to an embodiment of the invention.
Figure 2B:
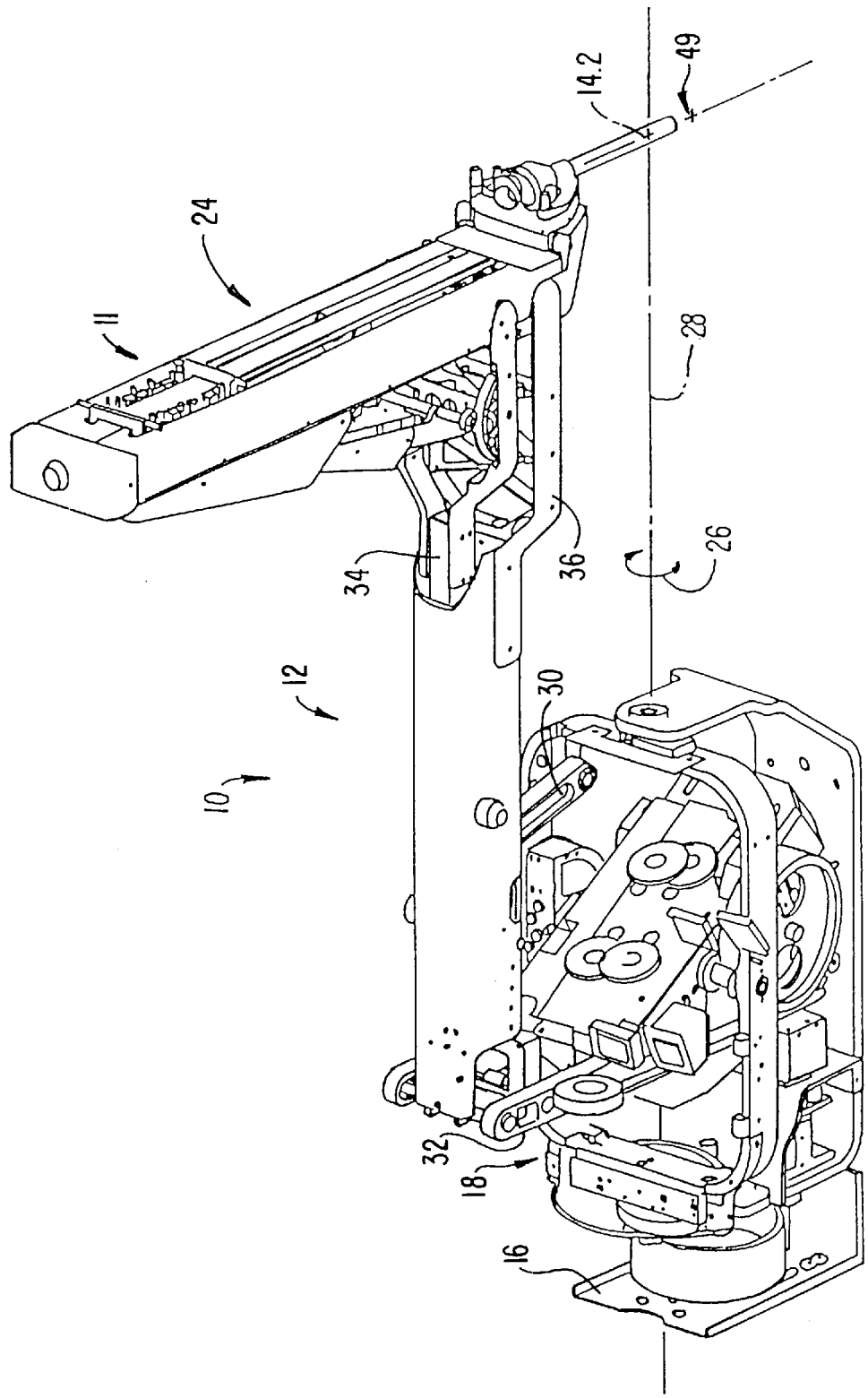
FIG. 2B is a perspective view of the robotic arm and surgical instrument assembly of FIG. 2A.
Figure 3:
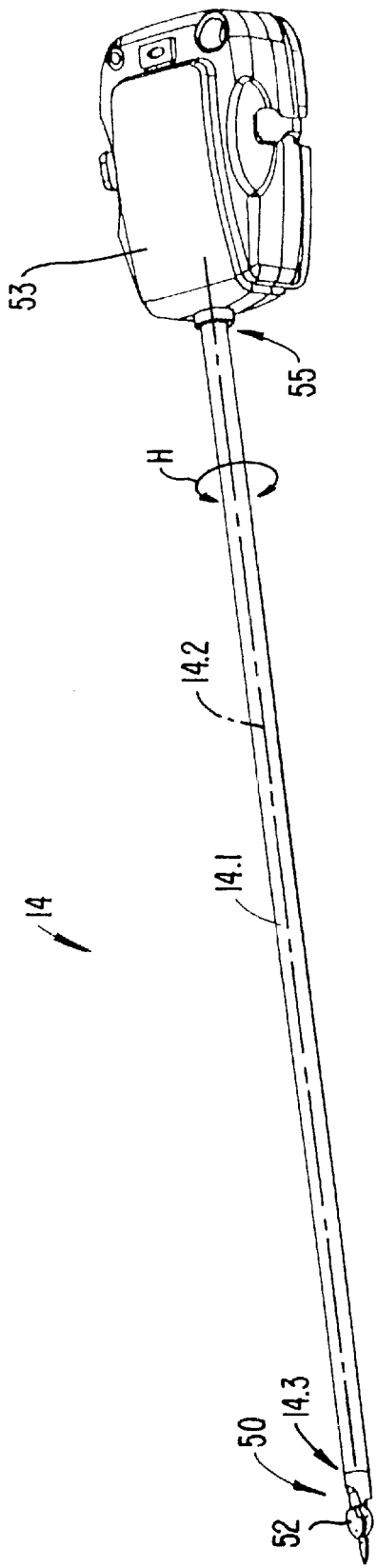
FIG. 3 is a perspective view of a surgical instrument according to an embodiment of the invention.

As shown in FIGS. 2A and 2B, each robotic arm assembly 10 includes an articulated robotic arm 12 and a surgical instrument 14 mounted thereon. As best seen in FIG. 3, the surgical instrument 14 includes an elongate shaft 14.1 and a wrist-like mechanism 50 located at a working end of the shaft 14.1. A housing 53, arranged releasably to couple the instrument 14 to the robotic arm 12, is located at an opposed end of the shaft 14.1. The shaft 14.1 is rotatably coupled to the housing 53 at 55 to enable angular displacement of the shaft 14.1 relative to the housing 53 as indicated by arrows H. In FIG. 2A, and when the instrument 14 is coupled or mounted on the robotic arm 12, the shaft 14.1 extends along an axis 14.2. The instrument 14 typically is releasably mounted on a carriage 11, which can be driven to translate along a linear guide formation 24 of the arm 12 in the direction of arrows P.

The robotic arm 12 is typically mounted on a base or platform at an end of its associated setup joint arm 95 by a bracket or mounting plate 16. The robotic arm 12 includes a cradle 18, an upper arm portion 20, a forearm portion 22, and the guide formation 24. The cradle 18 is pivotally mounted on the plate 16 in a gimbaled fashion to permit rocking movement of the cradle 18 in the direction of arrows 26 about a pivot axis 28 (FIG. 2B). The upper arm portion 20 includes link members 30, 32 and the forearm portion 22 includes link members 34, 36. The link members 30, 32 are pivotally mounted on the cradle 18 and are pivotally connected to the link members 34, 36. The link members 34, 36 are pivotally connected to the guide formation 24. The pivotal connections between the link members 30, 32, 34, 36, the cradle 18, and the guide formation 24 are arranged to constrain the robotic arm 12 to move in a specific manner.

Figure 4:
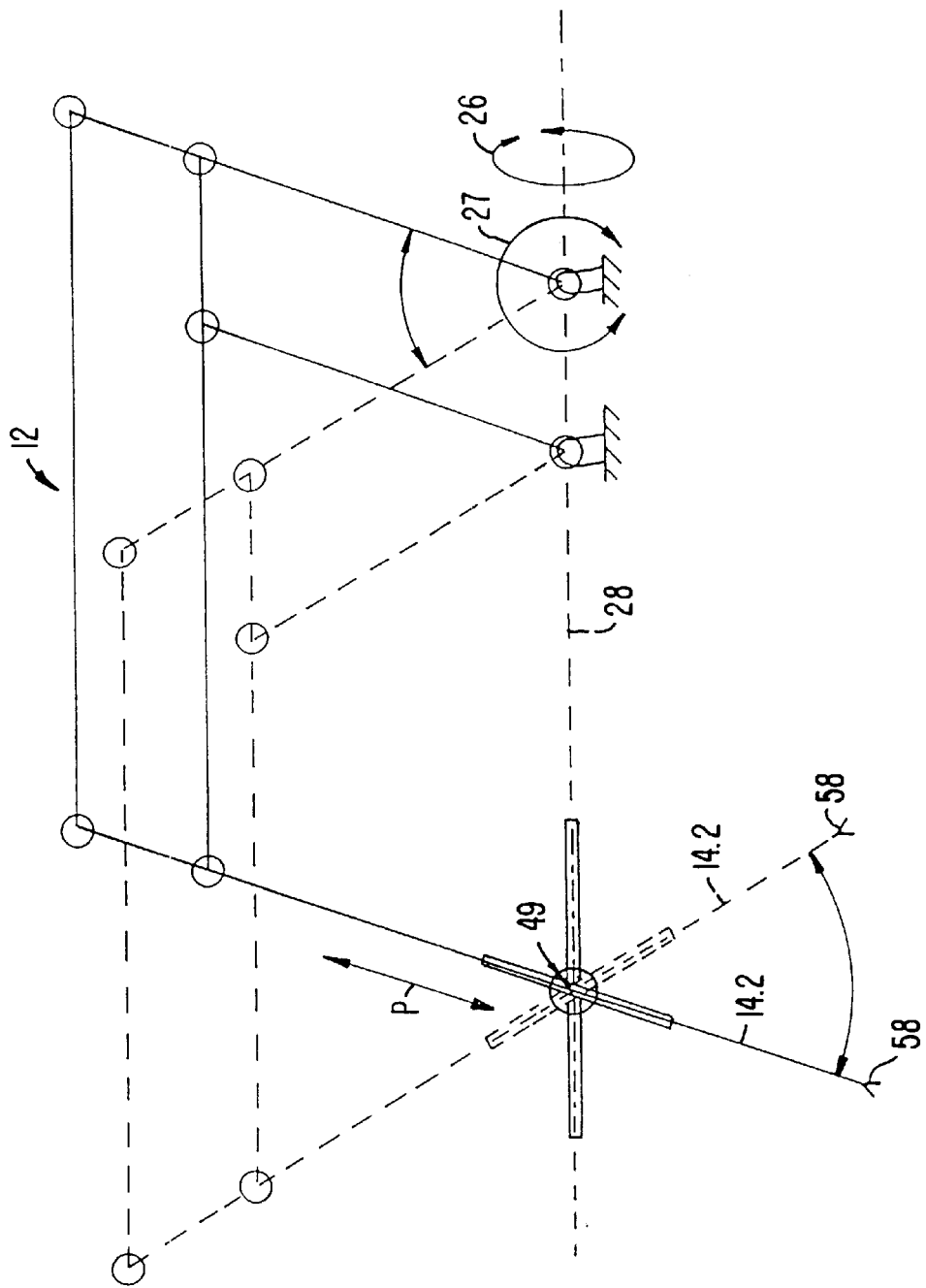
FIG. 4 is a schematic kinematic diagram corresponding to the side view of the robotic arm shown in FIG. 2A, and indicates the arm having been displaced from one position into another position.

The movements of the robotic arm 12 are illustrated schematically in FIG. 4. The solid lines schematically indicate one position of the robotic arm and the dashed lines indicate another possible position into which the arm can be displaced from the position indicated in solid lines.

It will be understood that the axis 14.2 along which the shaft 14.1 of the instrument 14 extends when mounted on the robotic arm 12 pivots about a pivot center or fulcrum 49. Thus, irrespective of the movement of the robotic arm 12, the pivot center 49 normally remains in the same position relative to the stationary cart 300 on which the arm 12 is mounted. In use, the pivot center 49 is positioned at a port of entry into a patient's body when an internal surgical procedure is to be performed. It will be appreciated that the shaft 14.1 extends through such a port of entry, the wrist-like mechanism 50 then being positioned inside the patient's body. Thus, the general position of the mechanism 50 relative to the surgical site in a patient's body can be changed by movement of the arm 12. Since the pivot center 49 is coincident with the port of entry, such movement of the arm does not excessively effect the surrounding tissue at the port of entry.

As can best be seen in FIG. 4, the robotic arm 12 provides three degrees of freedom of movement to the surgical instrument 14 when mounted thereon. These degrees of freedom of movement are firstly the gimbaled motion indicated by arrows 26, pivoting or pitching movement as indicated by arrows 27 and the linear displacement in the direction of arrows P. Movement of the arm as indicated by arrows 26, 27 and P is controlled by appropriately positioned actuators, e.g., electrical motors or the like, which respond to inputs from its associated master control to drive the arm 12 to a desired position as dictated by movement of the master control. Appropriately positioned sensors, e.g., potentiometers, encoders, or the like, are provided on the arm and its associated setup joint arm 95 to enable a control system of the minimally invasive telesurgical system to determine joint positions, as described in greater detail below. The term "sensors" as used herein is to be interpreted widely to include any appropriate sensors such as positional sensors, velocity sensors, or the like. By causing the robotic arm 12 selectively to displace from one position to another, the general position of the wrist-like mechanism 50 at the surgical site can be varied during the performance of a surgical procedure.

Figure 5:
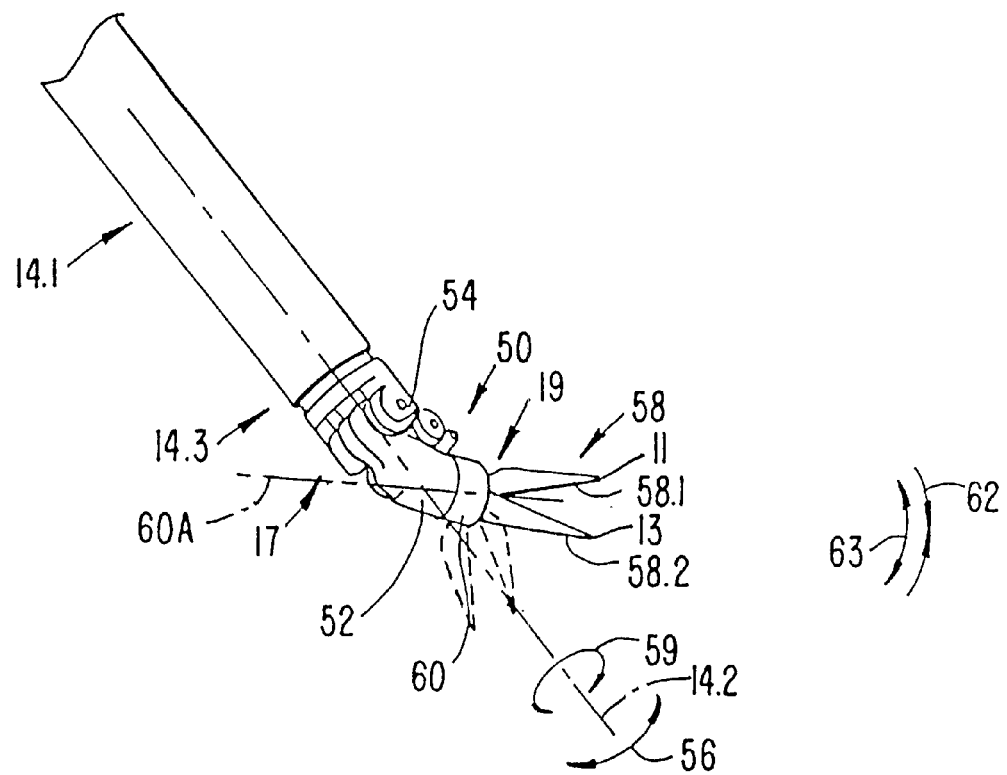
FIG. 5 is a perspective view of a preferred wrist member and end effector of the surgical instrument shown in FIG. 3, the wrist member and end effector being movably mounted on a working end of a shaft of the surgical instrument.

Referring now to the wrist-like mechanism 50 of FIG. 5, the working end of the shaft 14.1 is indicated at 14.3. The wrist-like mechanism 50 includes a wrist member 52. One end portion of the wrist member 52 is pivotally mounted in a clevis 17 on the end 14.3 of the shaft 14.1 by means of a pivotal connection 54. The wrist member 52 can pivot in the direction of arrows 56 about the pivotal connection 54. An end effector 58 is pivotally mounted on an opposed end of the wrist member 52. The end effector 58 has two parts 58.1, 58.2 together defining a jaw-like arrangement.

The end effector can be in the form of any desired surgical tool, e.g., having two members or fingers which pivot relative to each other, such as a clip applier for anchoring clips, scissors, two-fingered blunt dissection tools, forceps, pliers for use as needle drivers, or the like. Moreover, it can include a single working member, e.g., a scalpel, cautery electrode, or the like. When a different tool is desired during the surgical procedure, the tool 14 is simply removed from its associated arm and replaced with an instrument bearing the desired end effector.

In FIG. 5, the end effector 58 is pivotally mounted in a clevis 19 on an opposed end of the wrist member 52, by means of a pivotal connection 60. The free ends 11, 13 of the parts 58.1, 58.2 are angularly displaceable about the pivotal connection 60 toward and away from each other as indicated by arrows 62, 63. The members 58.1, 58.2 can be displaced angularly about the pivotal connection 60 to change the orientation of the end effector 58 as a whole, relative to the wrist member 52. Thus, each part 58.1, 58.2 is angularly displaceable about the pivotal connection 60 independently of the other, so that the end effector 58, as a whole, is angularly displaceable about the pivotal connection 60 as indicated in dashed lines in FIG. 5. Furthermore, the shaft 14.1 is rotatably mounted on the housing 53 for rotation as indicated by the arrows 59. Thus, the end effector 58 has three degrees of freedom of movement relative to the arm 12 in addition to actuation of the end effector members to, e.g., grip tissue, namely, rotation about the axis 14.2 as indicated by arrows 59, angular displacement as a whole about the pivot 60 and angular displacement about the pivot 54 as indicated by arrows 56. By moving the end effector within its three degrees of freedom of movement, its orientation relative to the end 14.3 of the shaft 14.1 can selectively be varied. Although preferred end effectors are both capable of rotating and of moving independently of one another, other end effectors within the scope of the present invention might be incapable of independent movement and/or at least one end effector member might be fixed in place relative to the wrist member and/or longitudinal shaft. The movement of the end effector relative to the end 14.3 of the shaft 14.1 is controlled by appropriately positioned actuators, e.g., electrical motors, or the like, which respond to inputs from the associated master control to drive the end effector 58 to a desired orientation as dictated by movement of the master control. Furthermore, appropriately positioned sensors, e.g., encoders, or potentiometers, or the like, are provided to permit the control system of the minimally invasive telesurgical system to determine joint positions.

Figure 6A:
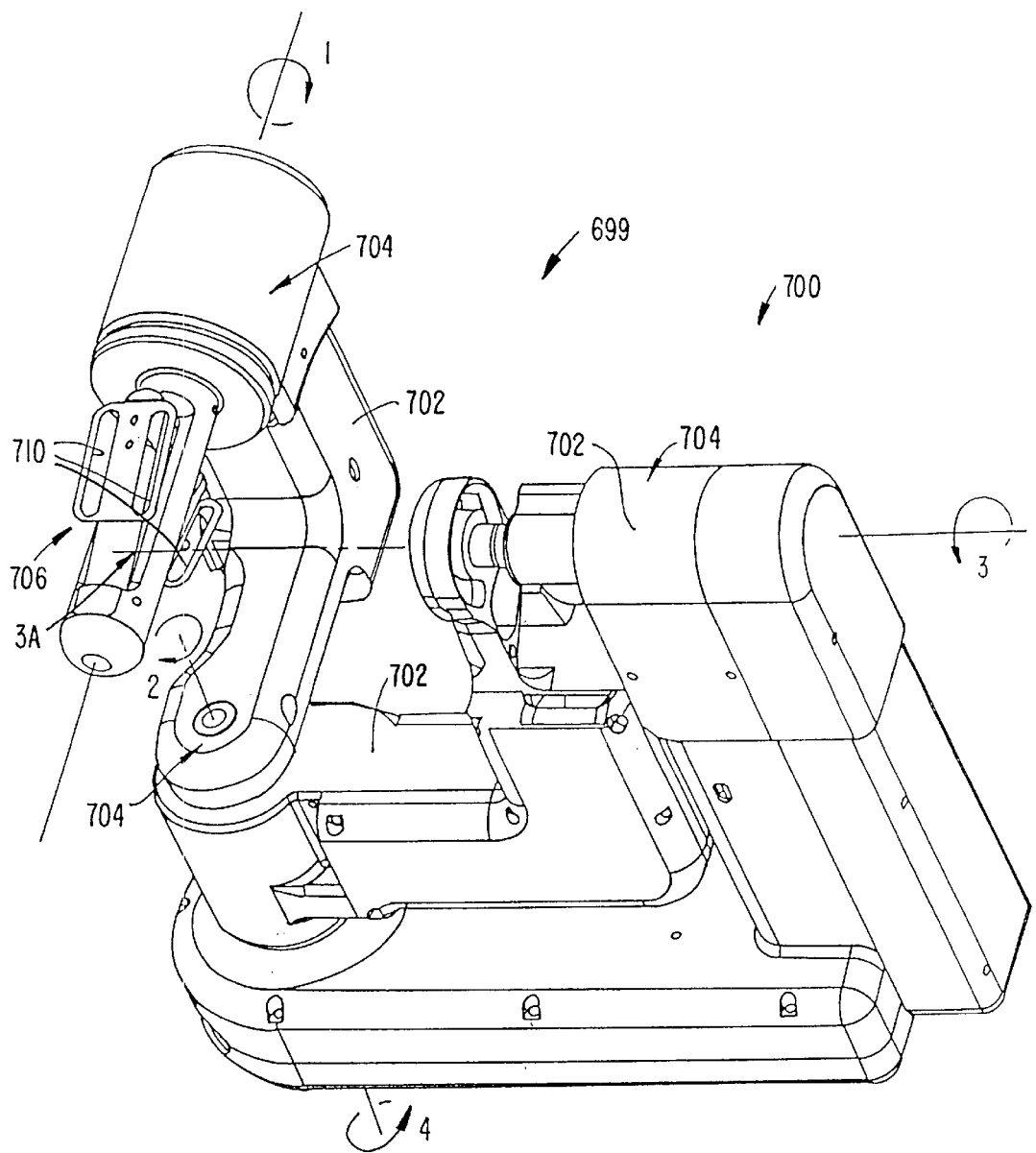
FIG. 6A is a perspective view of a hand held part or wrist gimbal of a master control device of the telesurgical system.
Figure 6B:
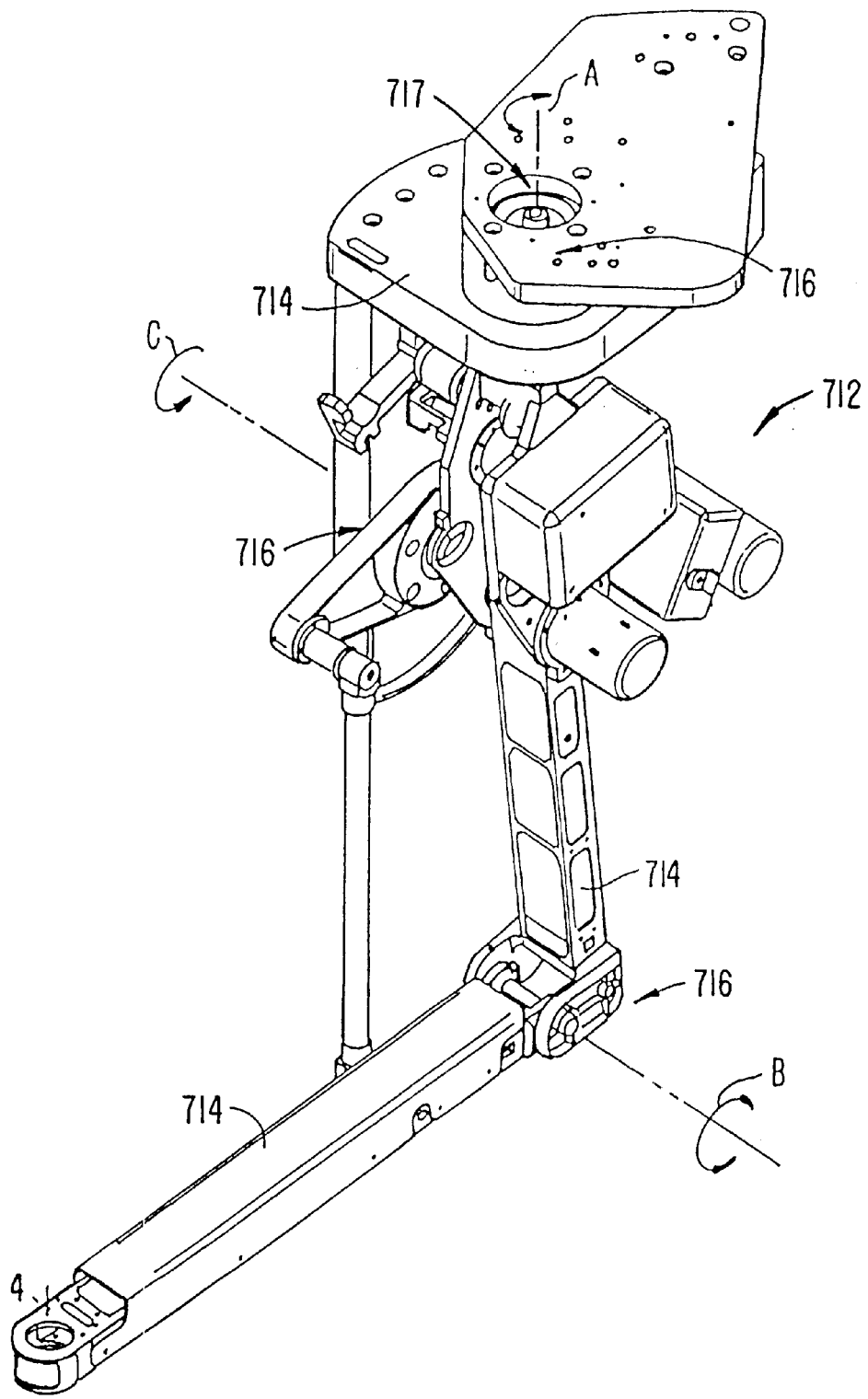
FIG. 6B is a perspective view of an articulated arm portion of the master control device of the telesurgical system on which the wrist gimbal of FIG. 6A is mounted in use.
Figure 6C:
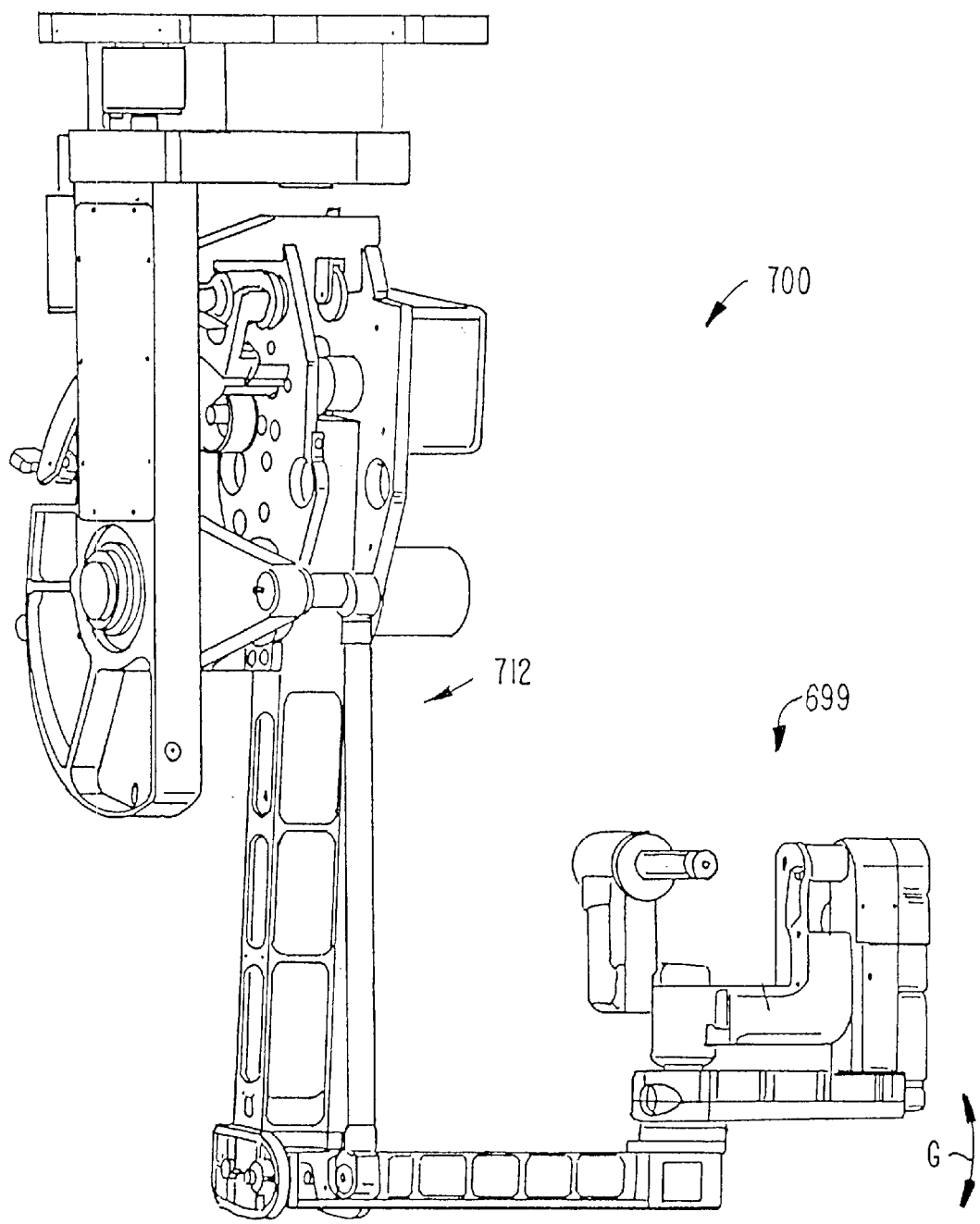
FIG. 6C is a perspective view of the master control device showing the wrist gimbal of FIG. 6A mounted on the articulated arm portion of FIG. 6B.

One of the master controls 700 is shown in FIG. 6C. As seen in FIG. 6A, a hand held part or wrist gimbal 699 of the master control device 700 has an articulated arm portion including a plurality of members or links 702 connected together by pivotal connections or joints 704. The surgeon grips the part 699 by positioning his or her thumb and index finger over a pincher formation 706. The surgeon's thumb and index finger are typically held on the pincher formation 706 by straps (not shown) threaded through slots 710. When the pincher formation 706 is squeezed between the thumb and index finger, the fingers or end effector elements of the end effector 58 close. When the thumb and index finger are moved apart the fingers of the end effector 58 move apart in sympathy with the moving apart of the pincher formation 706. The joints of the part 699 are operatively connected to actuators, e.g., electric motors, or the like, to provide for, e.g., force feedback, gravity compensation, and/or the like. Furthermore, appropriately positioned sensors, e.g., encoders, or potentiometers, or the like, are positioned on each joint 704 of the part 699, so as to enable joint positions of the part 699 to be determined by the control system.

The part 699 is typically mounted on an articulated arm 712 as indicated in FIG. 6B. Reference numeral 4 in FIGS. 6A and 6B indicates the positions at which the part 699 and the articulated arm 712 are connected together. When connected together, the part 699 can displace angularly about an axis at 4.

The articulated arm 712 includes a plurality of links 714 connected together at pivotal connections or joints 716. The articulated arm 712 further has appropriately positioned actuators, e.g., electric motors, or the like, to provide for, e.g., force feedback, gravity compensation, and/or the like. Furthermore, appropriately positioned sensors, e.g., encoders, or potentiometers, or the like, are positioned on the joints 716 so as to enable joint positions of the articulated arm 712 to be determined by the control system.

To move the orientation of the end effector 58 and/or its position along a translational path, the surgeon simply moves the pincher formation 706 to cause the end effector 58 to move to where he wants the end effector 58 to be in the image viewed in the viewer 202. Thus, the end effector position and/or orientation is caused to follow that of the pincher formation 706.

The master control devices 700, 700 are typically mounted on the station 200 through pivotal connections at 717 as indicated in FIG. 6B. As mentioned above, to manipulate each master control device 700, the surgeon positions his or her thumb and index finger over the pincher formation 706. The pincher formation 706 is positioned at a free end of the part 699 which in turn is mounted on a free end of the articulated arm portion 712.

The electric motors and sensors associated with the robotic arms 12 and the surgical instruments 14 mounted thereon, and the electric motors and sensors associated with the master control devices 700 are operatively linked in the control system. The control system typically includes at least one processor, typically a plurality of processors, for effecting control between master control device input and responsive robotic arm and surgical instrument output and for effecting control between robotic arm and surgical instrument input and responsive master control output in the case of, e.g., force feedback. An example of a suitable control system is described in U.S. application Ser. No. 09/373,678, entitled "Camera Referenced Control in a Minimally Invasive Surgical Apparatus", filed on Aug. 13, 1999.

II. In Vivo Accessories

To minimize the need to remove tools from the surgical site for tool replacement or instrument loading, the present invention provides ways to present a variety of accessories in vivo. The surgeon can manipulate these in vivo accessories using tools already in the surgical site and adapt them for performing different functions without the need to remove the tools from the surgical site. For accessories that need to be actuated to effect a predetermined treatment, the actuation can be performed remotely from outside the patient's body while placement of the accessories takes place at the surgical site by manipulating the accessories using robotic surgical tools at the site. A number of examples of such in vivo accessories are provided herein below.

A. Aortic Punch

In coronary artery bypass surgery, the goal is often to produce blood flow paths around the diseased areas of coronary arteries. A common procedure known as aortotomy involves forming an opening in the wall of an ascending aorta, and anastomosing a proximal end of a saphenous vein or the like to the opening. To form the opening in the wall of the aorta, the surgeon typically makes a linear incision in the aorta with a surgical scalpel, and then passes the anvil of an aortic punch through the incision and engage the punch to create an aortotomy.

Figure 7:
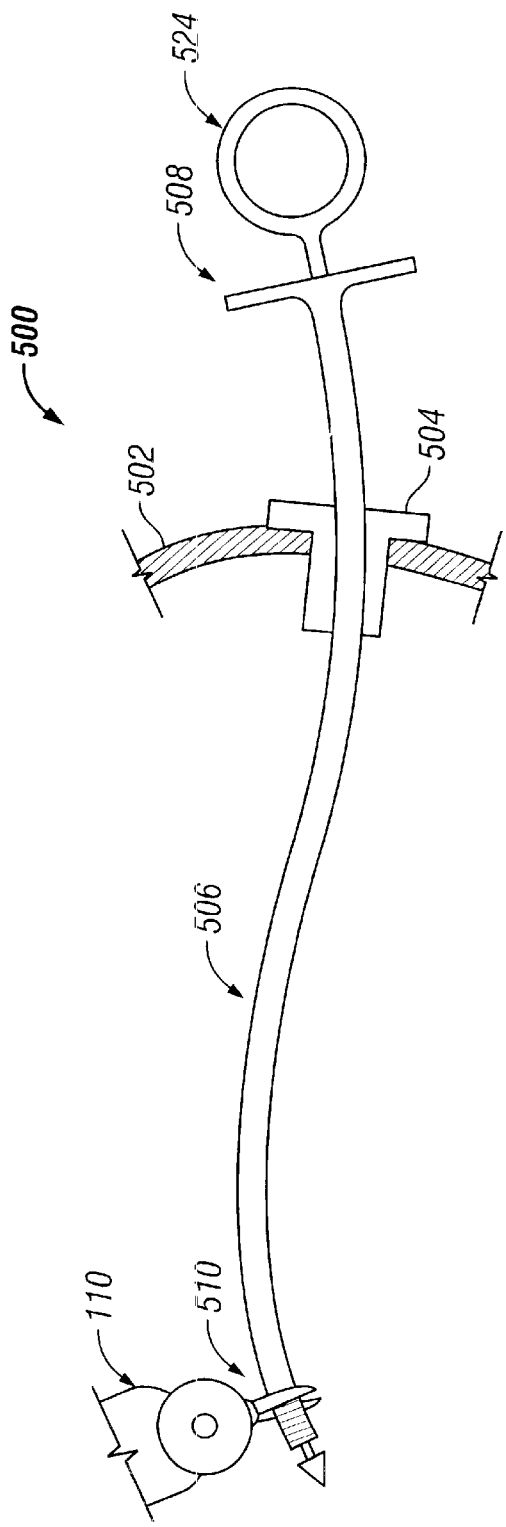
FIG. 7 is a schematic view of an aortic punch as an in vivo accessory.

FIG. 7 shows an aortic punch 500 introduced into the surgical site in the cavity of a patient via a port through the wall 502 of the patient's body. A cannula sleeve 504 is typically placed at the port. The aortic punch 500 desirably is sufficiently small in cross-section so that it can be inserted through a small cannula or directly into a needle stick hole. The aortic punch 500 desirably has a flexible body 506 including a proximal end 508 and a distal end 510. The proximal end 508 is disposed outside of the patient's body. The distal end 510 has a substantially rigid portion which can be securely grasped by a grasping tool having end effectors such as forceps 110 for manipulating the distal end 510 inside the surgical site as an in vivo accessory. The forceps 110 has two working members and is mounted on a wrist mechanism similar to the wrist mechanism 50 shown in FIGS. 3 and 5. The flexible body 506 allows the distal end 510 to be moved freely to the desired location by manipulating effectors on the surgical tool. By providing a non-self guiding punch or other in vivo accessory, and by relying on the surgeon's manipulation of the remotely controlled robotic tools to guide the accessory into position, costs can be saved on the accessories without losing any functionality. Precious time in the minimally invasive surgical procedure can also be saved by allowing the surgeon to position the accessory with an easier-to-use robotic surgical system rather than by struggling with a less intuitive control apparatus connected to the proximal end of the accessory outside the patient's body.

Figure 7A:
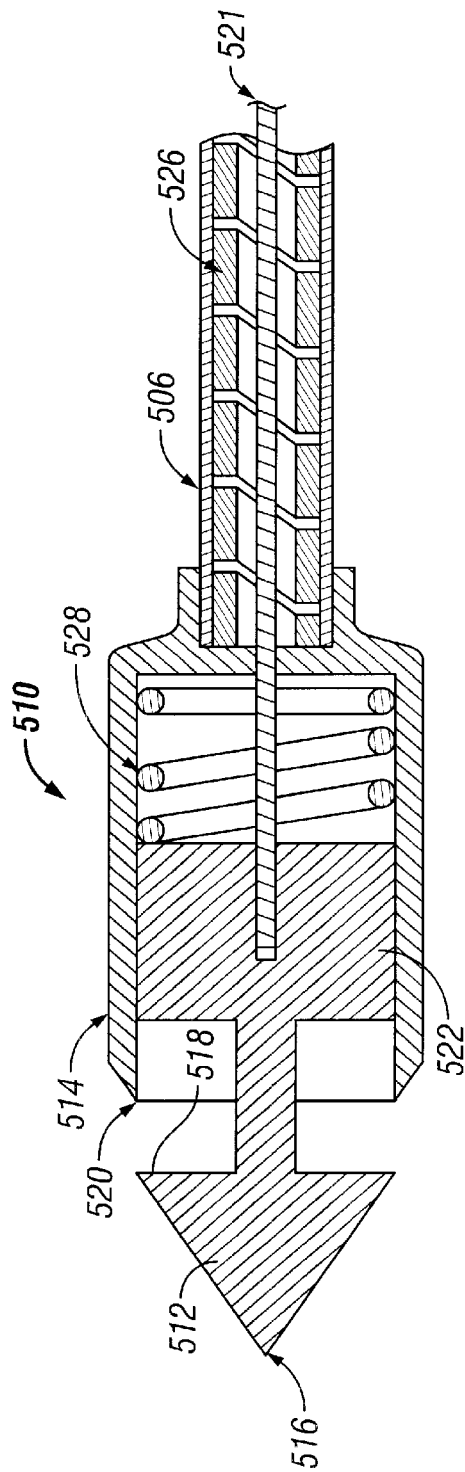
FIG. 7A is a cross-sectional view of the distal end of the aortic punch of FIG. 7.

As best seen in FIG. 7A, the distal end 510 includes an anvil 512 movable relative to a cutter 514. The cutter 514 has a generally cylindrical body with a cavity which partially houses the anvil 512. The anvil 512 has a distal point 516 for entering a scalpel cut in the aorta. The anvil 512 has a generally conical shape with an enlarged base 518. In use, the grasping tool 110 is used to insert the anvil 512 into the scalpel cut in the aorta. As the anvil 512 is retracted into the cavity of the cutter 514, the base 518 of the anvil 512 engages a cutting edge 520 to punch or cut an opening in the aorta.

The retraction of the anvil 512 is effected remotely by pulling an actuation cable 521 that is attached to the proximal end 522 of the anvil 512, as shown in FIG. 7A. The actuation cable 521 extends through the flexible body 506 to a handle 524 at the proximal end 508 of the aortic punch 500 (FIG. 7), so that the cable 521 is actuated from outside the patient's body. As seen in FIG. 7A, the flexible body 506 may include a flat wound flexible support 526 inside an outer shell or jacket. A return spring 528 is disposed in the cavity of the cutter 514 to resiliently bias the anvil 512 away from the cutter 514. Pulling the handle 524 overcomes the biasing force of the spring 528 to perform the punching of the aorta. Upon release of the handle 524, the spring biasing force returns the anvil 512 to the initial position away from the cutter 514.

The aortic punch 500 of FIGS. 7 and 7A is particularly beneficial for use in endoscopic procedures due to its small size so that it does not take up a lot of space inside the patient's body and can be introduced into the surgical site through a small cannula or a needle stick hole apart from the main incisions or ports required for the minimally invasive robotic surgical instruments and endoscope. In addition, in anticipation of its use during the surgical procedure, a surgeon's assistant, for example, can introduce the accessory into the patient's cavity so that the tool is ready for use by the surgeon as soon as desired. In these ways, a surgeon who has his desired surgical accessories already in vivo when needed may efficiently conduct a surgical procedure, rather than having to interrupt the flow of the procedure to change tools or wait for other necessary implements to be delivered to the surgical site. The aortic punch 500 advantageously can be made inexpensively, and may be used as a disposable accessory. It is appreciated that aortic punches having other configurations may be used. Moreover, the aortic punch 500 may be activated using other mechanisms.

B. Clamps

In a variety of surgical procedures, it is often necessary to isolate the heart or certain coronary blood vessels from the remainder of the circulatory system. Isolation is typically accomplished with a clamp device. For example, a cross clamp is used for completely occluding the aorta in a stopped heart procedure such as a stopped-heart coronary artery bypass surgery. In beating heart surgery, a side-biting clamp is typically used for occluding a part of the aorta where a proximal anastomosis is to be performed, although the use of the side-biting clamp for partially occluding the aorta can also be done in a stopped-heart procedure.

FIG. 8 shows a cross clamp 530 introduced into the surgical site in the cavity of a patient via a port through the wall 502 of the patient's body. The cross clamp 530 can be inserted via a small cannular sleeve 504 or through a needle stick hole in the wall 502. The cross clamp 530 desirably has a flexible body 532 including a proximal end 534 disposed outside the patient's body, and a distal end 536. The flexible body 532 may include a flat wound flexible support 537 inside an outer shell (FIG. 8A). The distal end 536 has a substantially rigid portion which can be securely grasped by a grasping tool 110 for manipulating the distal end 536 inside the surgical site as an in vivo accessory.

As illustrated in FIG. 8A, the distal end 536 includes a pair of clamp jaws 538, 540. In this embodiment, the jaw 538 is stationary and the jaw 540 is movable relative to the stationary jaw 538 by an actuation cable 542 which extends through the flexible body 532 to a handle 544 at the proximal end 534 of the clamp 530 (FIG. 8). A spring 546 is connected between the jaws 538, 540 to bias them apart toward an open position. In use, the grasping tool 110 is used to place the jaws 538, 540 around the aorta. Once the jaws are positioned at the desired location, at the request of the surgeon, the assistant may pull the handle 544 remotely on the cable 542 to move the movable jaw 540 to close the clamp 530 by overcoming the spring biasing force. Upon release of the handle 544, the spring 546 returns the movable jaw 540 to the open position.

In the embodiment shown in FIG. 8, a locking member such as a latch 548 is provided at the proximal end 534 of the cross clamp 530 for engaging teeth 549 on the handle 544 to locking the position of the handle 544 and cable 542, thereby fixing the relative positions of the jaws 538, 540. The locking feature conveniently locks the jaws 538, 540 in place after they have been positioned at the desired location and clamped around the aorta for occluding the aorta, thereby allowing the assistant to release the handle 544 and be free to perform other tasks. Inside the surgical site, once the clamp 530 is in place and locked, the surgeon may release the grip of the surgical tool 110 of the clamp 530 so that the surgical tool 110 can be used for the next task in the procedure.

It is understood that different clamp configurations may be used instead of the one illustrated in FIGS. 8 and 8A. For example, some clamps are configured to have jaws that are kept in a generally parallel arrangement between open and closed positions. It is further appreciated that other locking mechanisms may be used for locking the clamp 530. For instance, a spring-actuated mechanism may include a locking spring that biases the jaws together to close and lock the jaws. An operator can squeeze a trigger provided at the handle to open the jaws and place them around the aorta, and the operator can allow the spring to lock the jaws in place by releasing the trigger as desired.

Figure 9:
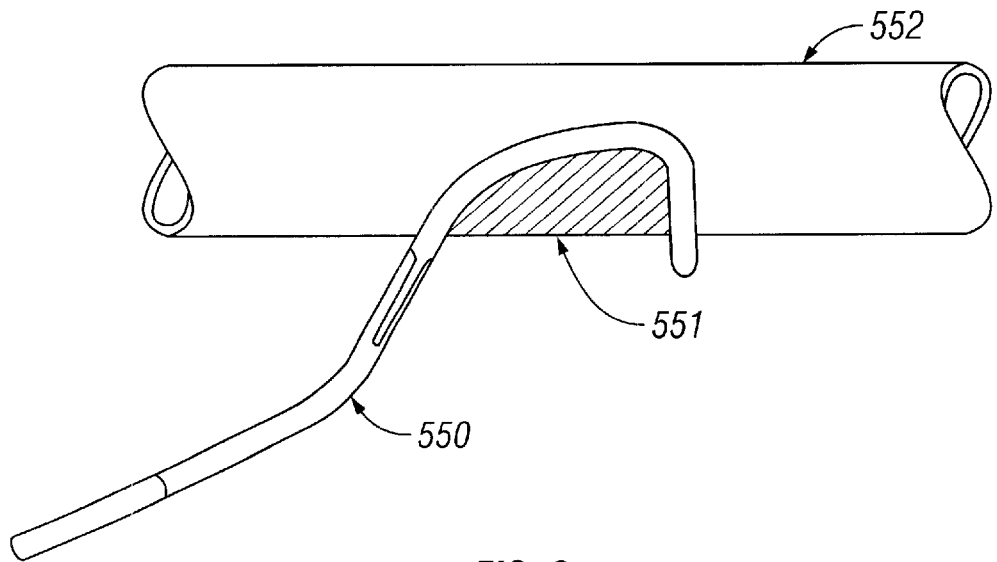
FIG. 9 is a schematic view of a conventional side-biting clamp used for partially occluding the aorta.

FIG. 9 shows a conventional side-biting clamp 550 that is typically used for occluding a portion 551 of the aorta 552. The side-biting clamp 550, however, has a big curve for blocking off a sufficiently large portion of the aorta 552 to allow it to be punched for performing anastomosis. The big curve of the clamp 550 is difficult to insert through a cannula, e.g., during a minimally invasive procedure.

Figure 10:
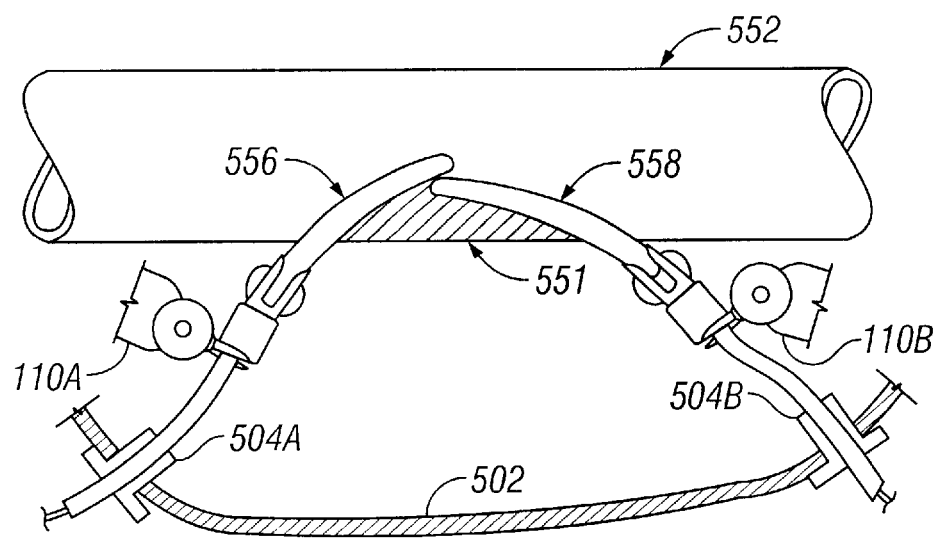
FIG. 10 is a schematic view of two clamps provided as in vivo accessories which are arranged to partially occlude the aorta.

An alternative to the side-biting clamp 550 involves the use of a pair of clamps as illustrated in FIG. 10. The first clamp 556 held by a first grasping tool 110A, and the second clamp 558 is held by a second grasping tool 110B. The jaws of the first clamp 556 and the jaws of the second clamp 558 are overlapped or placed adjacent to each other, typically at the tips, to enclose a region 551 of the aorta 552 to be occluded. The jaws of the clamps 556, 588 may be bent or curved as shown in FIG. 10, but they may also be straight. The jaws of the clamps 556, 558 do not have the big curves as the side-biting clamp 550 of FIG. 9, so that they may be more easily inserted via cannula sleeves 504A, 504B through the wall 502.

Figure 11A:
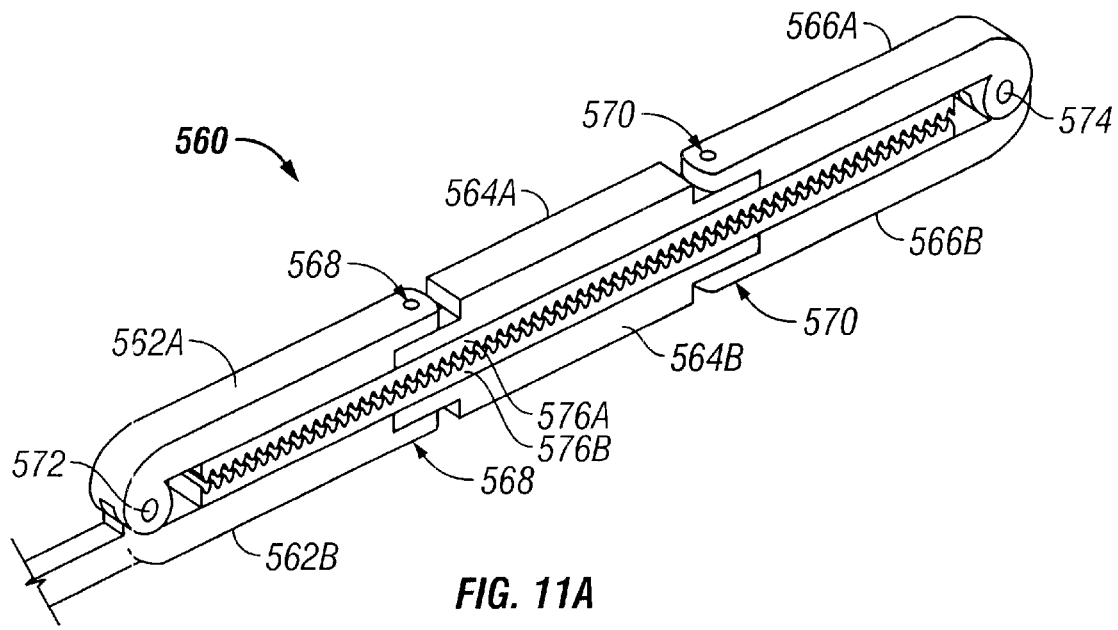
FIG. 11A is a perspective view of a foldable side-biting clamp in an extended position.
Figure 11B:
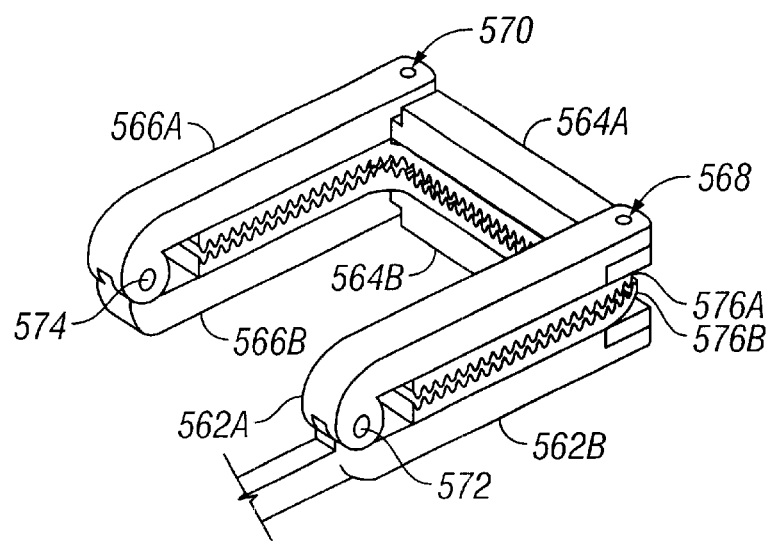
FIG. 11B is a perspective view of the foldable side-biting clamp in a folded position.

Another approach is to use a foldable side-biting clamp 560 which can enter the surgical site via a cannula in an extended position as shown in FIG. 11A, and be arranged into a folded configuration inside the surgical site to be used as a side-biting clamp as shown in FIG. 11B. The foldable clamp 560 has three pairs of links or arms: proximal arms 562A, 562B, middle arms 564A, 564B, and distal arms 566A, 566B. The proximal arms 562A, 562B are each connected, respectively, to the middle arms 564A, 564B via hinges 568, each of which are in turn connected, respectively, to the distal arms 566A, 566B via hinges 570. The hinges 568, 570 allow the arms to move between the extended position (FIG. 11A) and the folded position (FIG. 11B). The folding of the arms can be performed using a surgical tool in the surgical site or by actuating an internal mechanism in the clamp 560.

The proximal ends of the proximal arms 562A, 562B are connected at a pivot 572. The distal ends of the distal arms 566A, 566B are connected at another pivot 574. In the extended position of FIG. 11A, the three pairs of arms remain in a closed position, since the two pivots 572, 574 are not aligned but are spaced by the three pairs of arms. In the folded position of FIG. 11B, the proximal arms 562A, 562B and distal arms 566A, 566B are parallel to each other. The two pivots 572, 574 are aligned to permit pivoting of an upper jaw formed by the upper arms 562A, 564A, 566A relative to the lower jaw formed by the lower arms 562B, 564B, 566B. The pivoting can be carried out using any suitable mechanism, such as an actuation cable arrangement similar to that illustrated in FIG. 8A. The foldable clamp 560 of FIGS. 11A and 11B desirably includes upper and lower flexible members 576A, 576B made of a deformable material such as silicone rubber for providing a more secure grip of the aorta to prevent leakage. Of course, as with all of the surgical accessory devices disclosed herein, such occluding mechanism can be mounted on the distal end of a robotic, remotely controlled tool, preferably having a wrist joint to increase the number of degrees of freedom of distal movement, to further facilitate placement and movement at, and interaction with, the surgical site.

C. Heart Stabilizer

Figure 12:
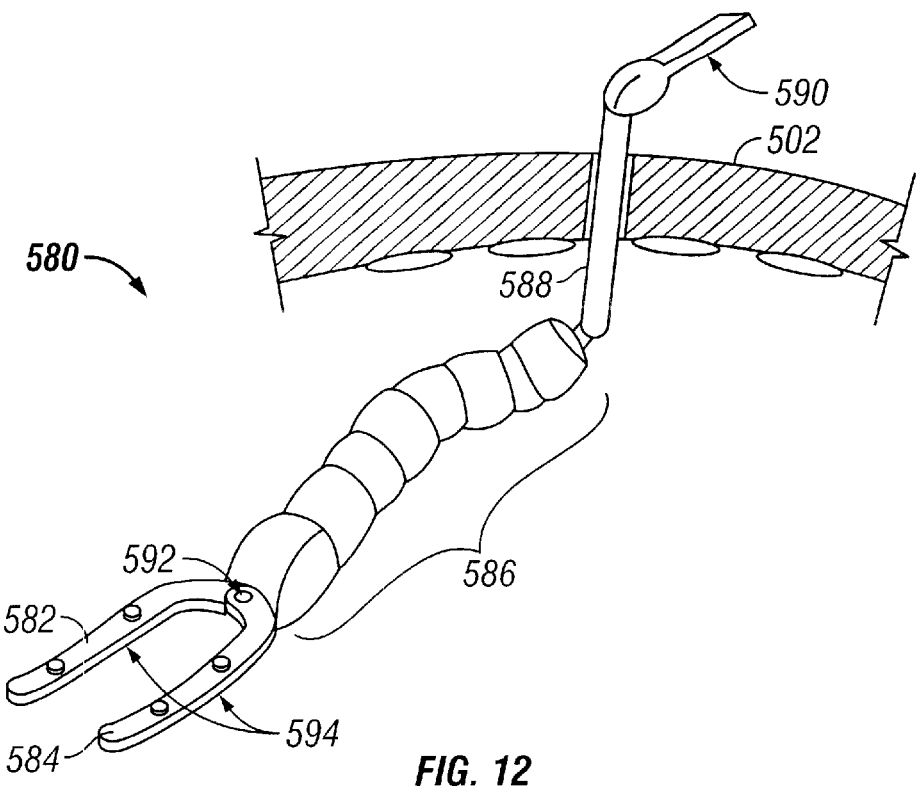
FIG. 12 is a perspective view of a stabilizer accessory.

In beating heart surgeries, a stabilizer is typically used to engage and stabilize a region of the heart. FIG. 12 shows a stabilizer accessory 580 including a bifurcated structure having first and second bodies 582, 584 coupled to each other and to an adjustable tail 586, which is connected to a stable member or post 588 extending through the wall 502 of the patient's body. A proximal control member 590 is coupled to the post 588 and disposed outside the patient's body. The tail 586 is configured to be adjustable to change shape in an unlocked mode, and to be fixed in position in a locked mode by actuating the proximal control member 590 remotely after the desired shape is obtained. The tail 586 typically includes a plurality of links that are adjustably connected in series An example of a tail 586 is a Mediflex® arm available from Mediflex®, a division of Flexbar Machine Corporation, Islandia, N.Y. The Mediflex® arm employs a chain of links that can be moved freely to any shape until it is actuated (e.g., by tightening with an actuation cable connected to the proximal control member 590) whereupon the arm becomes locked and maintains the position and orientation for stabilizing the heart or other tissues or organs.

Each of stabilizer bodies 582, 584 comprises an elongate plate extending distally from a pivot 592 to a distal end. One stabilizer body 582 may be stationary, while the other stabilizer body 584 is movable relative to the stationary body 582 using an arrangement similar to that shown for the clamp in FIG. 8A. In use, a grasping tool is used to place the stabilizer bodies 582, 584 with their tissue stabilizing surfaces 594 over a target region such as a region of the coronary artery of the heart. During beating heart surgery, the stabilizer 580 inhibits motion of the target region of the surgical worksite to allow treatment of target tissues. For more information on the preferred stabilizer end effectors and manners of activation/positioning, see copending U.S. patent application Ser. No. 09/436,524, entitled "Stabilizer for Robotic Beating Heart Surgery," filed on Nov. 9, 1999 and incorporated herein by reference in its entirety.

Figure 12A:
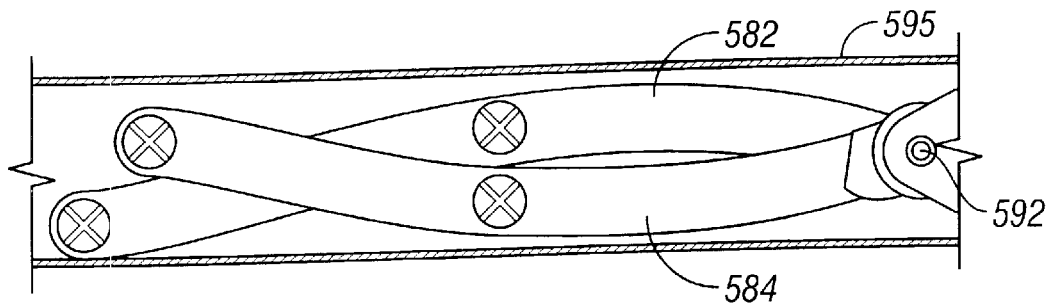
FIGS. 12A and 12B illustrate the stabilizer accessory of FIG. 12 in a small profile configuration for insertion into an internal surgical site via a cannula.
Figure 12B:
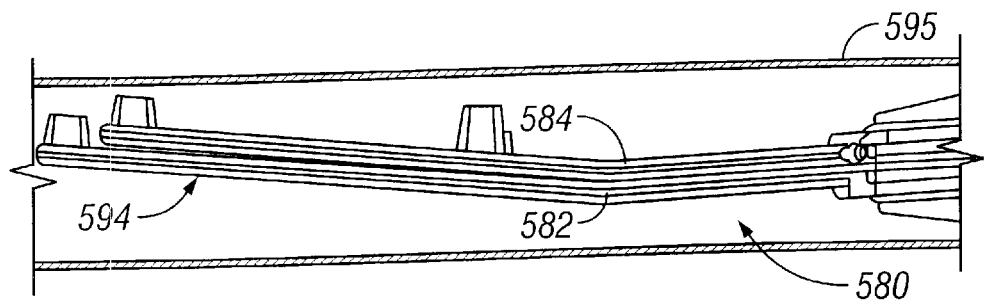

As seen in FIGS. 12A and 12B, each plate 582, 584 preferably bends laterally relative to its length in the direction of its width (so that the bodies 582, 584 cross distally of the pivot 592 when the stabilizer 580 is in a small profile configuration for insertion through a cannula 595) and in the direction of its thickness (as shown in FIG. 12B) so that the tissue stabilizing surfaces 594 of the bodies 582, 584 can engage a tissue surface without interference from the pivot 592 and tail 586. Although these multiple bends are preferred, to facilitate better delivery through smaller cannulas and better contact with the heart's surface, these bends should not be understood to limit the scope of the present invention.

Figure 12C:
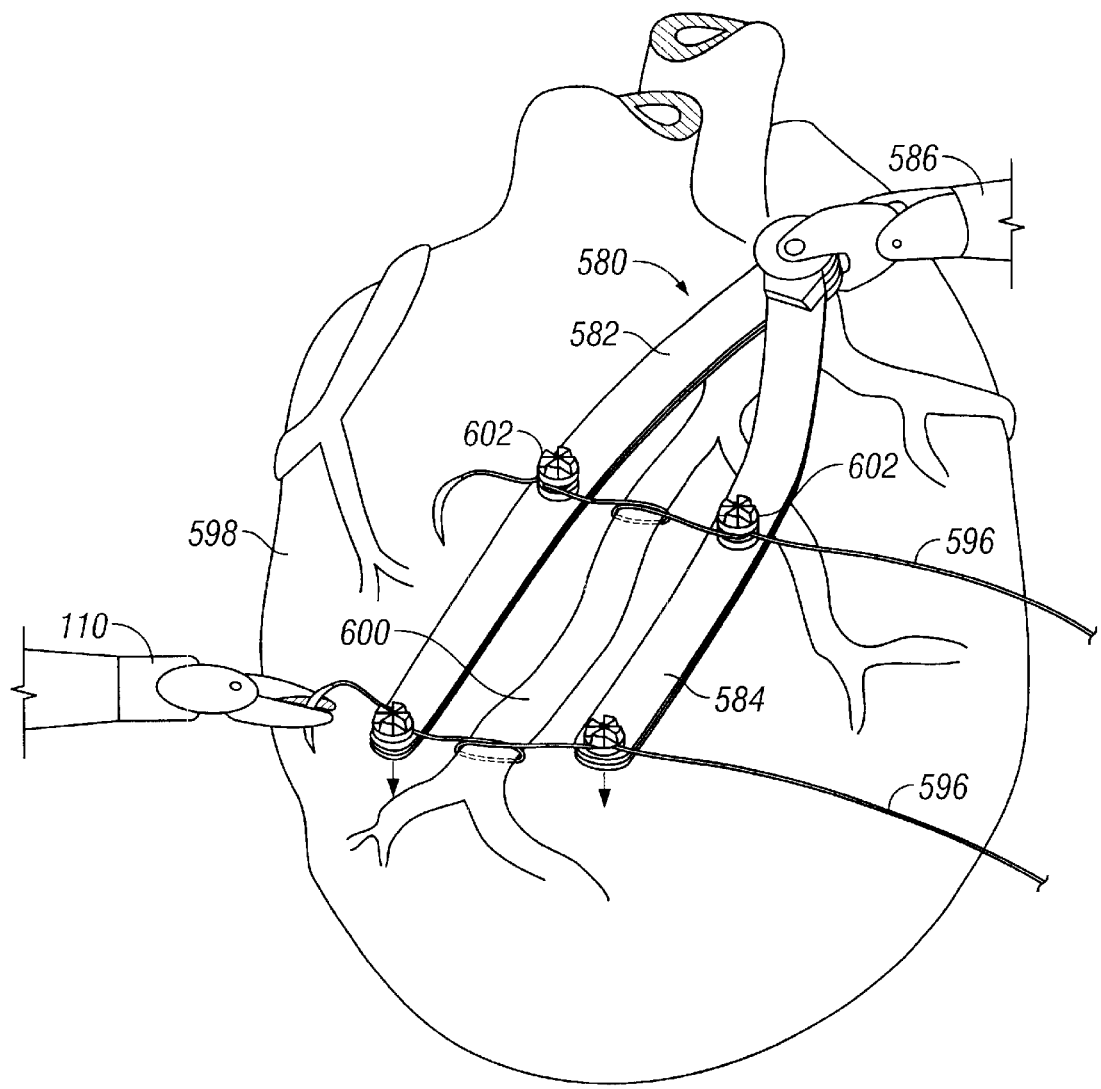
FIG. 12C shows the stabilizer accessory of FIG. 12 positioned over a target region of the heart to isolate a target region of a coronary artery for anastomosis.

A method for isolating a coronary artery CA downstream of an occlusion using the stabilizer 580 can be understood with reference to FIG. 12C. A pair of flexible member 596 is passed under and around the coronary artery CA using end effectors of a surgical tool 110. The stabilizer 580 is positioned against the heart 598 with the first and second bodies 582, 584 of the stabilizer positioned on two sides of the coronary artery CA so as to inhibit motion of the surgical worksite. A target region 600 of the coronary artery CA is isolated from upstream and downstream blood flow by tensioning flexible members 596 and tying the tensioned flexible members off to anchors 602 of stabilizer 580. Tying off the vessel in this manner not only permits isolation of the surgical site, but also can help to inhibit movement of the surgical worksite between the bodies 582, 584 during beating-heart surgery.

D. Clip Applier

Figure 13:
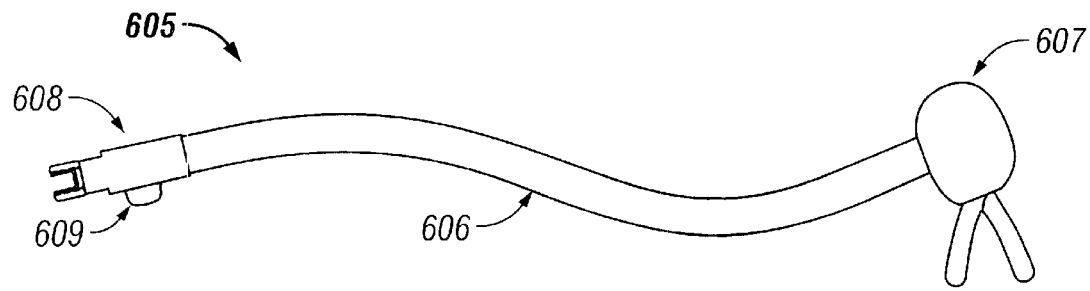
FIG. 13 is a schematic view of a multi-fire clip applier as an in vivo accessory.

FIG. 13 shows a multi-fire clip applier 605 having a body 606 with a proximal end 607 and a distal end 608. The body 606 is desirably flexible. The distal end 608 may include a rigid tab 609 that can be conveniently gripped by a grasping tool for moving the distal end 608 in the surgical site. The flexible body 606 allows the distal end 608 of the clip applier 605 to be moved freely and be placed at the desired location at the surgical site using the grasping tool disposed inside the surgical site for applying clips at the desired target location.

Figure 13A:
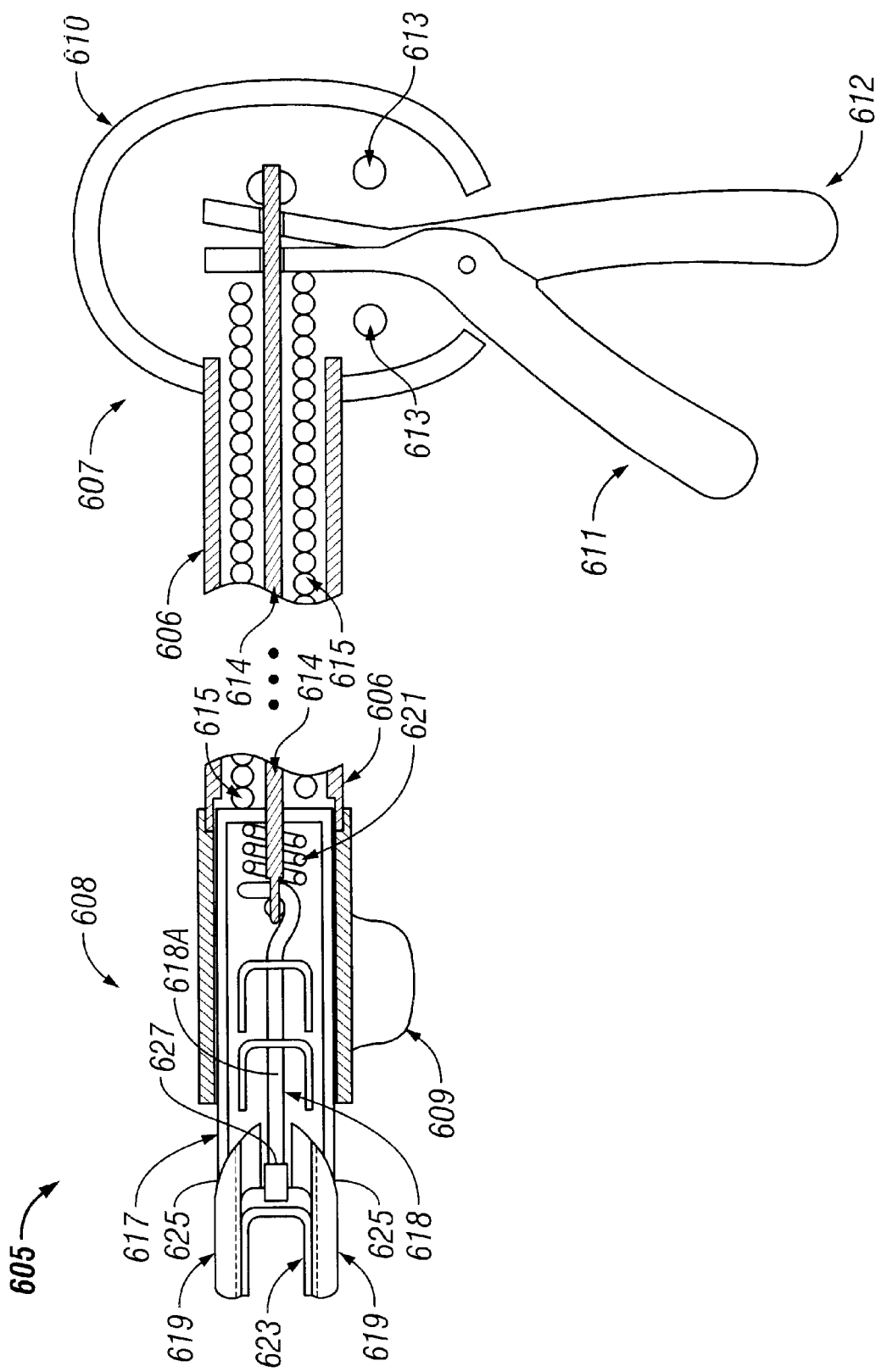
FIG. 13A is a partial cross-sectional view illustrating the distal end and proximal end of the clip applier of FIG. 13.

As best seen in FIG. 13A, the proximal end 607 includes a lever housing 610 having a push lever 611 and a pull lever 612 pivotally coupled together. The levers are partially disposed in and are supported by the lever housing 610. The lever housing 610 includes lever stops 613 defining the limit of the range of movement of the levers. The pull lever 612 is connected to a pull cable 614, while the push lever 611 is connected to a push sheath 615 around the pull cable 614. The cable 614 and sheath 615 are disposed in the flexible body 606.

The distal end 608 includes a clip applier housing 616. Disposed inside the clip applier housing 616 is a jaw squeezer 617 which is connected to the push sheath 615. The jaw squeezer 617 is a generally cylindrical member. A clip feeder 618 is disposed in the jaw squeezer 617. The proximal end of the clip feeder 618 is connected to the pull cable 614. The distal end of the clip feeder 618 slides between a pair of clip applier jaws 619. A spring (not shown) biases the jaws 619 apart. The jaws can slide perpendicularly to the axis of the housing. A spring 621 inside the jaw squeezer 617 biases the clip feeder 618 to pull the jaw squeezer 617 back from the jaws 619. The jaw squeezer 617 forms a clip storage region for storing therein a plurality of clips 623 that can be advanced one-by-one toward the jaws 619 to be applied to a target region such as tissue.

The jaws 619 include an inclined or ramped outer surface 625 for contacting the jaw squeezer 617. When the push lever 611 and pull lever 612 are squeezed together at the proximal end 607, the push lever 611 moves the push sheath 615 to push the jaw squeezer 617 outward relative to the clip applier housing 616, while the pull lever 612 pulls the pull cable 614 to pull the clip feeder 618 inward. As the jaw squeezer 617 moves out, the contact between the jaw squeezer 617 and the ramped surface 625 of the jaws 619 cause the jaws 619 to close, thereby squeezing the clip 623 to apply the clip 623.

The clip feeder 618 has a ramped surface 618A that ramps up from the proximal end adjacent the pull cable 614 toward the distal end adjacent the jaws 619, terminating at a ratchet-like catch 627. As the clip feeder 618 is pulled into the jaw squeezer 617, the next clip 623 in the jaw squeezer 617 rides on the ramped surface 618A of the clip feeder 618 until it engages the catch 627. The clip feeder 618 advances clips to the jaws 619 in a ratchet-like manner. Upon releasing the push lever 611 and the pull lever 612, the jaw squeezer 617 moves inward toward the clip applier housing 616, while the clip feeder 618 moves outward away from the jaw squeezer 617. The catch 627 advances the next clip 623 to load it between the jaws 619 ready for application to the next target region.

It is appreciated that the same principles of the clip applier may be applied to other similar surgical instruments such as surgical staplers (for applying staples) and tackers (for applying surgical tacks) within the scope of the present invention.

E. Needle Extractor

Figure 14:
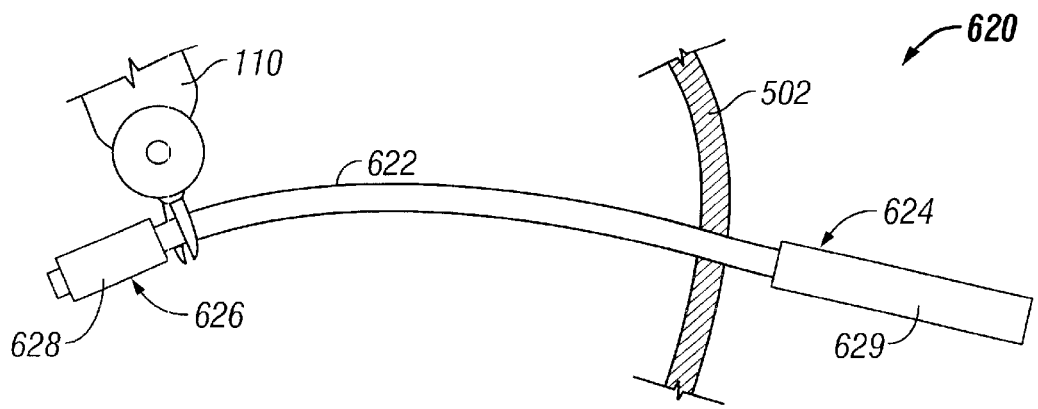
FIG. 14 is a schematic view of a magnetic extraction member as an in vivo accessory.

FIG. 14 shows an extractor tool 620 for extracting metallic objects such as needles or the like from the body cavity of the patient. The extractor tool 620 desirably includes a flexible or malleable body 622 having a proximal end 624 and a distal end 626. The distal end 626 includes a magnetic member 628, and is introduced into the surgical site via a port through the wall 502 of the patient's body. The distal end 626 has a substantially rigid portion. The proximal end 624 includes a handle 629 disposed outside the patient's body. The handle 629 can be controlled to activate the magnet 628 at the distal end 626 to form a magnetic field for attracting metallic members.

In use, a grasping tool 110 is used to grasp the distal end 626 to maneuver it within the surgical site. The magnet 628 at the distal end 626 may be activated remotely from outside the patient's body to attract metallic objects such as loose or dropped needles, clips, or staples, and extract them from the surgical site. The magnetic extractor tool 620 is particularly effective in extracting objects such as needles that may be difficult to grasp with conventional grasping tools.

F. In Vivo Actuation Member

The above in vivo accessories typically include actuation members such as actuation cables that are integral with or built into the accessories. In the following examples, the actuation member for actuating the in vivo accessory is a separate member that is typically introduced into the surgical site via a separate port.

Figure 15:
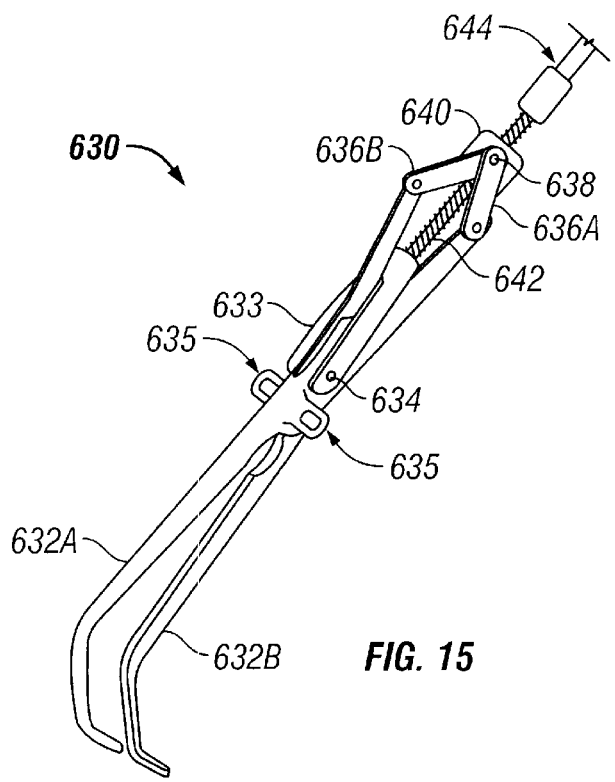
FIG. 15 is a perspective view of a pair of pliers as an in vivo accessory.

FIG. 15 shows an in vivo accessory including a pair of pliers 630. The pliers 630 include arms 632A, 632B at a distal end that are pivotally connected to a housing 633 to rotate about a pivot 634 in a jaw-like manner to move between open and closed positions. The housing 633 may include grab bars 635 that can be more conveniently grasped by a grasping tool in the surgical site. The arms 632A, 632B are each pivotally connected to a drive link 636A, 636B, which are coupled at a common pivot 638 on a drive nut 640. The drive nut 640 is threadingly coupled to a threaded shaft 642, which is rotatably coupled to the housing 633. The arms 632A, 632B open as the drive nut 640 moves down the shaft 642 toward the arms at the distal end, and close as the drive nut 640 moves up the shaft 642. The movement of the drive nut 640 up and down the threaded shaft 642 is produced by rotating the shaft 642 relative to the housing 633. For instance, rotating the shaft 642 in one direction causes the drive nut 640 to move up the shaft, while rotating the shaft 642 in the opposite direction causes the drive nut 640 to move down the shaft. The drive nut 640 and threaded shaft 642 desirably form a non-backdrivable mechanism that stays tight or fixed relative to each other until the shaft 642 is rotated.

Figure 15A:
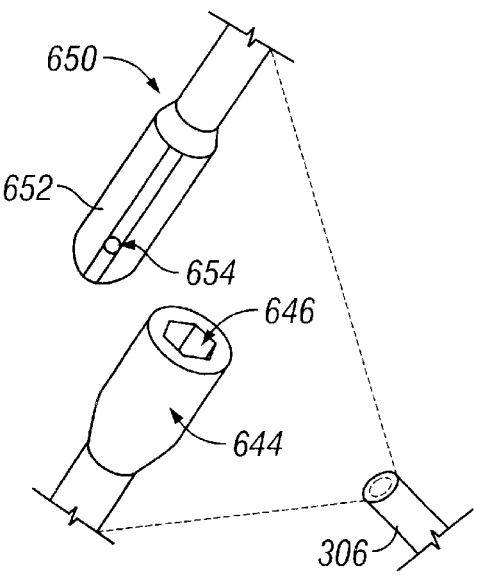
FIG. 15A is a perspective view of a separate in vivo actuation member for engaging and actuating the pliers of FIG. 15.

At the proximal end of the threaded shaft 642 is a docking member 644. As best seen in FIG. 15A, the docking member 644 has a cavity 646 for receiving a rotational actuator 650 configured to rotate the shaft 642 to actuate the arms 632A, 632B. The cavity 646 has a hexagonal shape, but may be shaped differently in other embodiments to form a docking cavity. The rotational actuator 650 includes a distal drive member 652 that is configured to be inserted into the cavity 646 of the docking member 644 and to dock or mate with the docking member 644 for applying a rotational force to control movement of the arms 632A, 632B. The actuator 650 is a separate in vivo accessory that is preferably introduced into the surgical site via a separate port such as a needle stick hole through a wall of the patient. The actuator 650 may have a substantially rigid body or more desirably a flexible body that allows the distal drive member 652 to be manipulated and maneuvered more freely inside the surgical site. The distal drive member 652 is detachably coupled to the docking member 644, and is controlled remotely from outside the surgical site when desired to adjust the pliers 630. The torque needed to rotate the actuator 650 can be generated remotely from outside the patient's body.

In the embodiment of FIG. 15A, the distal drive member 652 can be adjusted to lock onto the docking member 644. The locking mechanism employs a detent ball 654 that can be moved forward to cause the distal member 652 to expand when the distal member 652 is inserted into the cavity 646 of the docking member 644 to lock the distal member 652 with the docking member 644. To unlock the distal member 652 from the docking member 644, the detent ball 654 is retracted to allow the distal member 652 to contract for removal. The movement of the detent ball 654 may be controlled by a cable connected between the detent ball 654 and a control button at the proximal end of the actuator 650 which can be manipulated from outside the patient's body to remotely adjust the position of the detent ball 654.

In use, a grasping tool is used to grasp the pliers 630 (e.g., at the grab bars 635) and place the arms 632A, 632B at the target location. Another grasping tool can be used to insert the distal drive member 632 of the rotational actuator 630 into the cavity 646 of the docking member 644 for docking. The actuation member 650 can be easily and accurately positioned in a field of view of a scope 306 for engaging and actuating the pliers 630. The detent ball 654 in the actuator 650 may be actuated remotely from outside the surgical site to move forward to lock the distal drive member 652 with the docking member 644, so that the grasping tool for the distal drive member 652 can be released and used for performing the next task if desired. The rotational actuator 650 is remotely actuated from outside the surgical site to rotate the distal drive member 652 to drive the threaded shaft 642 of the pliers 630 in rotation to move the drive nut 640 up or down the shaft 642, thereby adjusting the positions of the arms 632A, 632B of the pliers 630 to perform a desired function at the target location. After the proper adjustments are made to the arms 632A, 632B, the actuator 650 may be disengaged from the pliers 630, and the grasping tool may also be detached from the pliers 630. Disengaging the actuator 650 from the pliers 630 frees up space at the surgical site. This may be advantageous to the surgeon who may desire the surgical site to be as uncluttered as possible during a surgical procedure.

Figure 16:
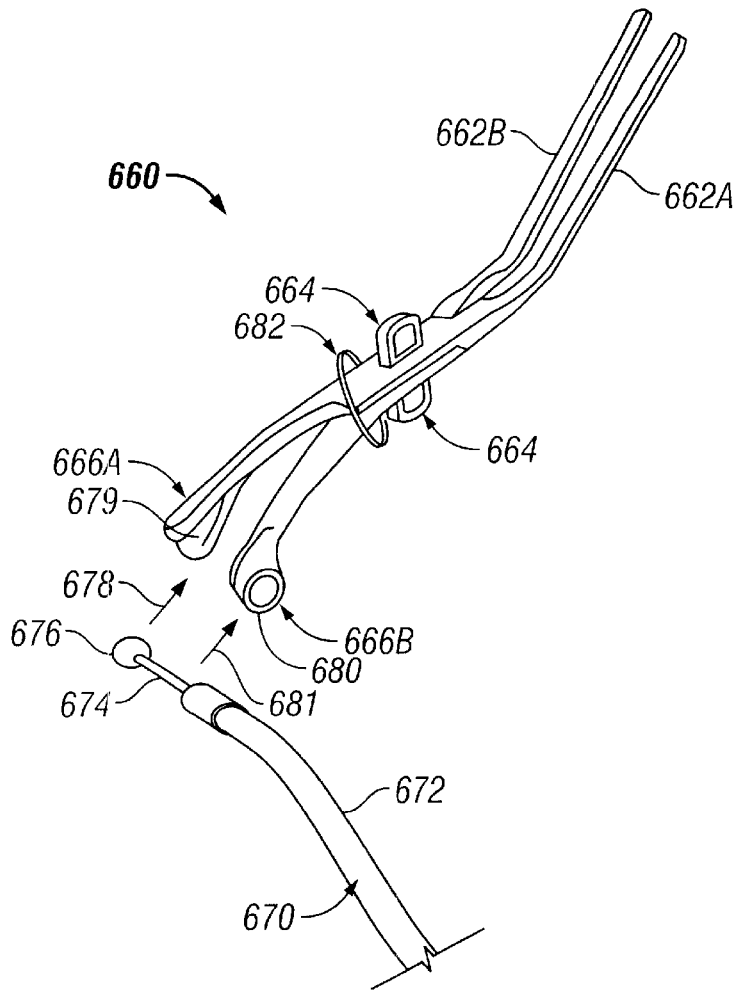
FIG. 16 is a perspective view of another pair of pliers controlled by another actuation member provided as an in vivo accessory.

In another embodiment shown in FIG. 16, the pliers 660 have a pair of arms 662A, 662B that are pivotably coupled, and may include grab bars 664. The proximal ends of the arms 662A, 662B include docking members 666A, 666B for docking an actuation member 670. The actuation member 670 includes a body 672 that may be rigid but is desirably flexible. An actuation cable or push rod 674 is slidable within the body 672. A distal member 676 is connected to the distal end of the cable 674. The distal member 676 shown is a ball, but it may be shaped different in other embodiments. The cable 674 is actuated remotely from the proximal end of the actuation member 670 disposed outside the patient's body.

Figure 16A:
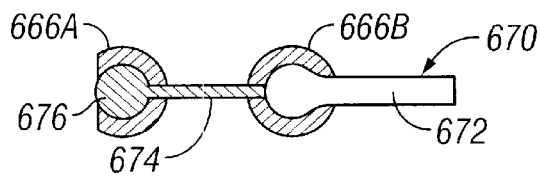
FIG. 16A is a schematic view illustrating the engagement between the actuation member and the pliers of FIG. 16.

To dock the actuation member 670, the distal ball 676 enters the cavity in the docking member 666A from the proximal end in the direction indicated by arrow 678. The docking member 666A has a side slit or slot 679 for accommodating the cable 674 as the ball 676 enters the cavity. Similarly, the other docking member 666B has a cavity and a side slit or slot 680 for receiving the actuation cable 674 and the end of the body 672 in the direction indicated by arrow 681. In the docked position, the distal ball 676 is engaged with one docking member 666A and the end of the actuation member body 672 is engaged with the other docking member 666B, as best seen in FIG. 16A. Moving the distal ball 676 away from the body 672 causes the arms 662A, 662B to open in a jaw-like manner, while pulling the distal ball 676 toward the body 672 causes the arms 662A, 662B to move to a closed position.

Typically, the actuation member 670 is used to adjust the arms 662A, 662B to grip a target tissue by moving them from an open position toward a closed position. After the desired grip is produced, a lock ring 682 (FIG. 16) can be slid down the arms 662A, 662B to lock them in place to maintain the grip. The actuation member 670 can then be disengaged from the pliers 660, and be available for performing the next task as desired.

Figure 16B:
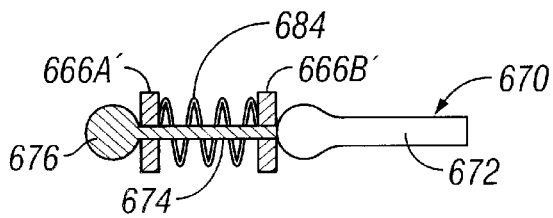
FIG. 16B is a schematic view illustrating the engagement between an actuation member and pliers according to another embodiment.

In an alternate embodiment, the arms 662A, 662B are biased to open by a spring 684, as shown in FIG. 16B. Because the spring 684 applies a biasing force to open the arms, the actuation member 670 need actuate the arms in only one direction to bring them toward one another to the closed position. The docking members 666A', 666B' of the arms 662A, 662B may be configured differently for docking the actuation member 670 for actuating only to close the arms. As seen in FIG. 16B, the docking members 666A', 666B' may include slots to allow the actuation cable 674 to slide in for engagement. Because the actuation member body 672 and the distal ball 676 are disposed on opposite sides of the docking members 666A', 666B', pulling the distal ball 676 toward the body 672 moves the arms 662A, 662B toward one another against the spring force. When the ball 676 is moved away from the body 672, the actuation member 670 does not apply a force on the arms, but the biasing force of the spring 684 moves the docking members 666A', 666B' apart.

The pliers 630 or 670 may be introduced into the surgical site in any suitable way. For instance, each accessory can be connected to a cable and inserted through an opening into the surgical site and be removed from the site by pulling on the cable from outside the patient's body. Alternatively, an accessory support can be used to introduce a plurality of accessories into the surgical site.

Figure 17:
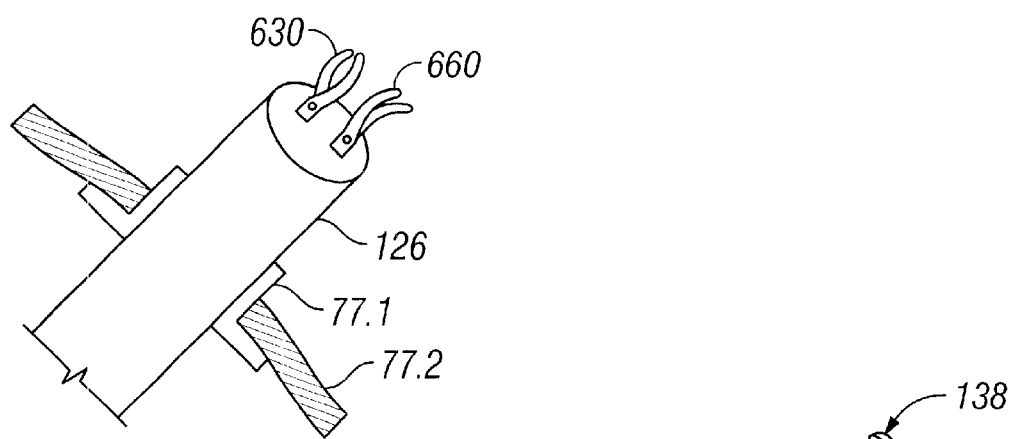
FIG. 17 is a perspective view of a surgical accessory support block.

FIG. 17 illustrates a surgical accessory support in the form of a block 126 for holding the accessories such as the pliers 630, 660. The block 126 is introduced through the cavity wall 77.2 via a cannula sleeve 77.1. The support block 126 in one embodiment is made of a foam material or the like which deflects to releasably secure the accessories therein. The accessories can be removed by the grasping tool 110 inside the surgical site to perform a desired treatment and then returned to the block 126 after use.

Figure 18:
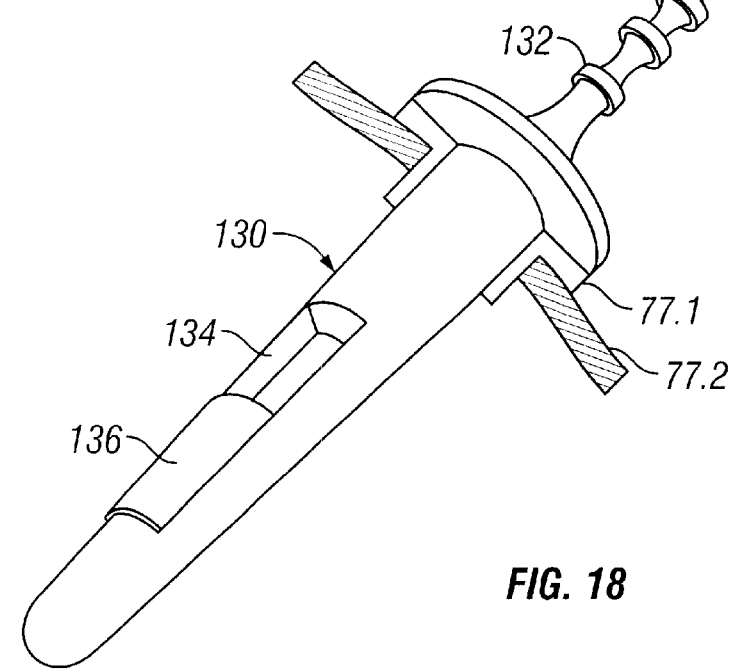
FIG. 18 is a perspective view of a surgical accessory container.

FIG. 18 shows a container or box 130 as another embodiment of a surgical accessory support. The box 130 extends through the cavity wall 77.2 via a cannula sleeve 77.1. A handle 132 supports the box 130 in the surgical site from outside the patient's cavity. The box 130 includes a compartment 134 for housing accessories and a door 136 which can be opened to allow access to the accessories, and be closed during transportation of the box 136 into and out of the surgical site. A variety of mechanisms can be used to control movement of the door 136. In the embodiment shown, a control rod 138 is connected with the door 136 and extends through the end of the handle 132. The control rod 138 allows the operator to open the door 136 by pushing the rod 138 toward the handle 132 and to close the door 130 by pulling the rod 138 away from the handle 132. A physical or solenoid-activated latch might be included to lock the door in an open configuration during an operation, if desired. It is appreciated that other devices can be used for introducing the surgical accessories into the surgical site and supporting them therein.

Figures 19A, 19B:
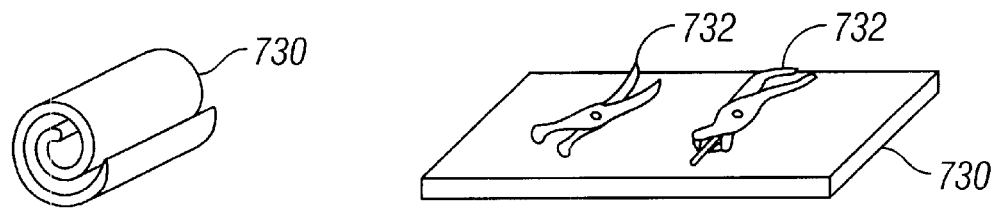
FIG. 19A is a perspective view of a surgical accessory support belt in a deflated state according to another embodiment of the invention.
FIG. 19B is a perspective view of the surgical accessory support belt of FIG. 19A in an inflated state.

In another embodiment as shown in FIG. 19A, an inflatable tool belt or support 730 can be used to hold accessories 732 such as pliers, and can be inserted into the surgical site through a port with the tool belt 730 in a deflated state. The accessories 732 may be releasably attached to the tool belt 730 in any suitable manner, such as the use of velcro or the like. After the tool belt 730 has been inserted into the surgical site, it can be inflated in a manner similar to a balloon catheter to expose the accessories 732 so that they may be used in the surgical site, as illustrated in FIG. 19B. The inflated tool belt 730 provides support for the accessories 732 and may cause the accessories to stand in an erect position, making them more easily graspable by a grasping tool such as forceps 110 or the like. The tool belt 730 can be deflated for retraction. A mechanism similar to those used for balloon catheters can be used for inflating and deflating the tool belt 730.

G. Ultrasound Catheter

Figure 20A:
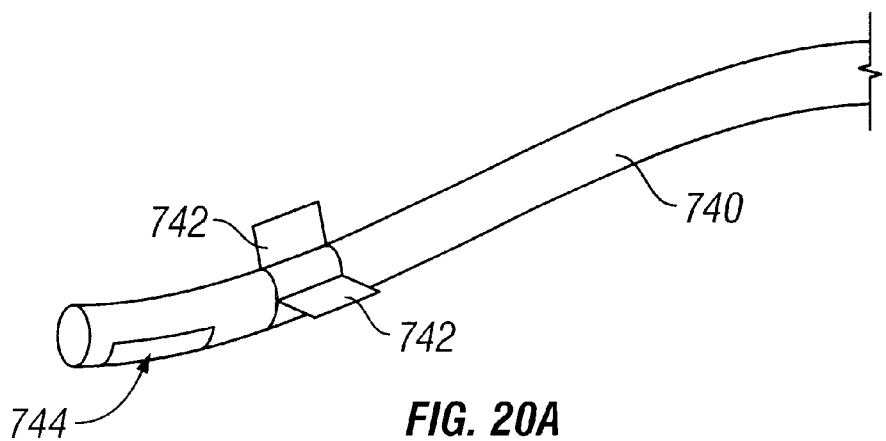
FIGS. 20A and 20B show perspective and end views of a modified ultrasound catheter for grasping and guidance by a robotic tool at the surgical site to collect ultrasound images of the surgical site.
Figure 20B:
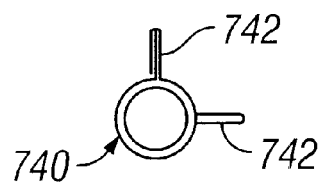

Shown in FIGS. 20A and 20*b* is another embodiment of an in vivo accessory within the scope of the present invention. Known ultrasound catheters, such as available from Acuson of Mountain View, Calif., are available for insertion into body cavities or body lumens to image body tissues. These catheters typically have some sort of proximal control mechanism for maneuvering the distal catheter tip around the cavity or lumen to capture ultrasound images. This kind of remote control typically requires the somewhat awkward movement of multiple knobs, levers or dials to indicate the desired direction of movement of the catheter tip.

However, when used in conjunction with a robotic surgical system in which robotic tools are already present at the surgical site, capturing ultrasound images becomes possible without having to "remotely" control the ultrasound catheter for movement with hardware located on the proximal end of the catheter outside the patient's body. Instead, the catheter 740 as shown in FIGS. 20A and 20B may simply be inserted into the thorax, for example, through a small incision or port between the ribs as an in vivo accessory, for the robotic surgeon to grasp with one or more instruments already present at the surgical site. The surgeon is then able to move the catheter along the vessel or tissue of interest by manipulating the robotic surgical system to move the catheter 740, rather than either relying on an assistant to directly control movement of the ultrasound system or having to relinquish control of the robotic system to turn his attention to the ultrasound system.

The surgeon's ability to maneuver the catheter around the surgical site can be improved by providing one or more tabs or grab bars 742 towards the distal end of the catheter 740, preferably proximal of the active detector portion 744 of the ultrasound catheter 740 but within a short distance (e.g., less than about 5 cm) of the distal tip, which bars or tabs 742 can be used to facilitate grasping contact between the end effectors and the catheter 740. Multiple grab bars or other grasping aids such as slots or end effector "gloves" mounted on the catheter 740 can be provided with different orientations, to permit the surgeon to manipulate the catheter while maintaining a comfortable orientation of the robotic system's master controls. Two grab bars 742 are shown in FIGS. 20A and 20B. The simple grab bars 742 comprise brass crimped around the catheter to provide a "flag" to which the end effectors can couple.

Figure 20C:
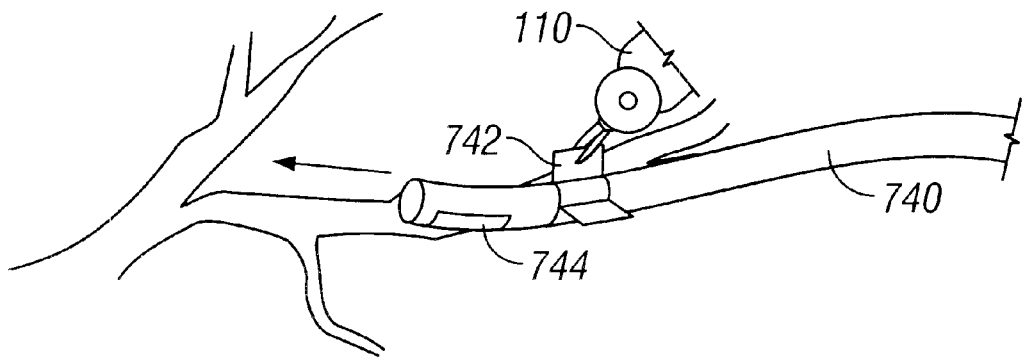
FIG. 20C shows the modified ultrasound catheter of FIGS. 20A and 20B being manipulated by the robotic surgical system at a surgical site in an embodiment of the invention.

FIG. 20C shows an ultrasound catheter 740 being manipulated by a robotically controlled end effector 10 around a surgical site, and more specifically along a coronary artery on the surface of a patient's heart, in the manner of a preferred embodiment of the invention. For more information on this concept, see copending U.S. patent application Ser. No. 09/464,455, entitled "Devices and Methods for Presenting and Regulating Auxiliary Information on an Image Display of a Telesurgical System to Assist an Operator in Performing a Surgical Procedure," filed on Dec. 14, 1999 and incorporated herein by reference in its entirety.

The above-described arrangements of apparatus and methods are merely illustrative of applications of the principles of this invention and many other embodiments and modifications may be made without departing from the spirit and scope of the invention as defined in the claims. For instance, other telesurgical systems, e.g., without a remote center of motion, and surgical tools can be used to perform surgery with the in vivo accessories. The examples of surgical accessories and ways of presenting them in vivo are illustrative and not exhaustive. Additional illustrative examples of surgical accessories that can be provided in vivo in accordance with the present invention include various end effectors.

Furthermore, other in vivo tools can also be introduced into the body cavity and manipulated by robotic tools already in the cavity, as described throughout this application. For example, irrigating tubes providing carbon dioxide or saline to the surgical site, suction devices, and blowing devices can each be introduced to the surgical site through small accessory ports in the patient's body wall, to be manipulated at the surgical site by the end effectors of other robotic tools controlled remotely by the surgeon. These tools can be actuated from outside the body cavity, either by the surgeon's assistant when requested, or by the surgeon him/herself by actuating an accessory input device such as an on/off switch operatively coupled to the accessory. Alternatively, an illumination source, such as an optical fiber bundle, in addition to or instead of the illumination source on a typical endoscope, can be introduced as an accessory to further illuminate the surgical site. Similarly, a flexible camera or other imaging device might be introduced through a separate port to be manipulated by the surgeon at the surgical site, to provide further visual information about the patient's anatomy that is not as viewable as desired in the main endoscopic image, such as anatomy hidden from view by other anatomy or objects. Further, as described in U.S. patent application Ser. No. 09/464,455, entitled "Devices and Methods for Presenting and Regulating Auxiliary Information on an Image Display of a Telesurgical System to Assist an Operator in Performing a Surgical Procedure", filed Dec. 14, 1999, additional visual information about hidden anatomy can be provided to the surgeon during the surgical procedure by utilizing the picture-in-picture capability described therein.

Other "active" accessories can also be introduced to the surgical site, manipulated into position inside the body by the surgeon, and activated either inside or outside the body once correctly positioned. For example, pacing electrodes can be introduced into the heart tissue minimally invasively in this manner, as can an aortic cannulation system. No large opening is required to place these devices or achieve these results because of the dexterity provided to the surgeon directly at the surgical site, despite the surgeon's only access to the site being through small, minimally invasive ports.

The scope of the invention should, therefore, be determined not with reference to the above description, but instead should be determined with reference to the appended claims along with their full scope of equivalents.

What is claimed is:

1. A method of performing minimally invasive robotic surgery in a body cavity of a patient, the method comprising:
   introducing at least one non-robotic surgical accessory into the cavity, the accessory not coupled to an end effector of a robotic surgical tool when introduced;
   introducing a robotic surgical tool into the cavity;
   coupling the surgical accessory with the robotic surgical tool inside the cavity after separately introducing the surgical accessory and the robotic surgical tool into the cavity; and
   actuating the surgical accessory from outside the cavity of the patient to effect a predetermined treatment.

2. The method of claim 1 wherein the surgical accessory includes a member movable between a rest position and an actuated position, and wherein actuating the surgical accessory comprises moving the movable member toward the actuated position.

3. The method of claim 2 wherein the movable member of the surgical accessory is coupled with an actuation member having a proximal portion disposed outside of the cavity of the patient, and wherein actuating the surgical accessory comprises manipulating the actuation member to move the movable member from outside the cavity of the patient.

4. The method of claim 3 wherein the actuation member is introduced into the cavity separately from the surgical accessory, and wherein the actuation member is detachably coupled with the movable member of the surgical accessory inside the cavity.

5. The method of claim 2 further comprising locking the movable member of the surgical accessory in the actuated position.

6. The method of claim 5 wherein actuating the surgical accessory comprises connecting the surgical accessory with a portion of the body cavity of the patient in the actuated position, and locking the movable member of the surgical accessory in the actuated position comprises maintaining connection of the surgical accessory with the portion of the body cavity.

7. The method of claim 6 further comprising, prior to actuating the surgical accessory, positioning the surgical accessory with the robotic surgical tool to a target region for effecting the predetermined treatment at the target region, and further comprising, after locking the movable member of the surgical accessory in the actuated position, decoupling the surgical accessory from the robotic surgical tool inside the cavity.

8. The method of claim 1 wherein actuating the surgical accessory comprises advancing a clip from a clip storage region to a clip applying region of the surgical accessory and applying the clip to a target region.

9. The method of claim 1 wherein actuating the surgical accessory comprises punching an opening in a tissue in the body cavity of the patient.

10. The method of claim 1 wherein actuating the surgical accessory comprises at least partially occluding a vessel in the body cavity of the patient.

11. The method of claim 1 wherein actuating the surgical accessory comprises stabilizing a target region of the body cavity of the patient.

12. The method of claim 1 wherein actuating the surgical accessory comprises generating a magnetic field to attract metallic objects inside the body cavity to the surgical accessory.

13. The method of claim 1 wherein the robotic surgical tool is manipulated by a servomechanism from outside the cavity to couple the robotic surgical tool with the surgical accessory inside the cavity.

14. The method of claim 13 wherein the robotic surgical tool is connected with a robot arm which is disposed outside the cavity and robotically controlled to manipulate the robotic surgical tool.

15. The method of claim 1 wherein the surgical accessory is coupled with the robotic surgical tool by grasping the surgical accessory with the robotic surgical tool.

16. The method of claim 1 wherein the surgical accessory is coupled with the robotic surgical tool by mating the surgical accessory with the robotic surgical tool to form a mated connection.

17. The method of claim 1 further comprising positioning the surgical accessory with the robotic surgical tool to a target region for effecting the predetermined treatment at the target region.

18. The method of claim 1 wherein the at least one surgical accessory is introduced into the cavity through a cannula.

19. The method of claim 1 wherein the at least one surgical accessory is introduced into the cavity supported by a surgical accessory support, and is removable from the surgical accessory support within the cavity.

20. The method of claim 19 wherein the surgical accessory support includes a container.

21. The method of claim 19 wherein the surgical accessory support includes at least a portion of an elongate shaft of a second robotic surgical tool.

22. The method of claim 21 wherein the movable member of the surgical accessory is coupled with an actuation member having a proximal portion disposed outside of the cavity of the patient, and wherein actuating the surgical accessory comprises manipulating the actuation member to move the movable member from outside the cavity of the patient.

23. The method of claim 1 further comprising decoupling the surgical accessory from the robotic surgical tool inside the cavity.

24. The method of claim 23 wherein the surgical accessory is supported by a surgical accessory support which is introduced into the cavity before the surgical accessory is coupled with the robotic surgical tool inside the cavity, and wherein the decoupled surgical accessory is returned to the surgical accessory support inside the cavity.

25. The method of claim 23 wherein a plurality of surgical accessories are introduced into the cavity, the method further comprising coupling another surgical accessory inside the cavity with the robotic surgical tool after the decoupling step.

26. The method of claim 1 wherein two clamp accessories are introduced into the cavity, and wherein actuating the clamp accessories comprises clenching the clamp accessories around portions of an aorta with the clamp accessories in contact to enclose a region of the aorta, thereby partially occluding the aorta.

27. A method of performing minimally invasive robotic surgery in a body cavity of a patient, the method comprising:

introducing at least one non-robotic surgical accessory into the cavity, the accessory not coupled to an end effector of a robotic surgical tool when introduced;

introducing a robotic surgical tool into the cavity;

coupling the surgical accessory with the robotic surgical tool inside the cavity after separately introducing the surgical-accessory and the robotic surgical tool into the cavity;

manipulating the robotic surgical tool from outside the body cavity of the patient to position the surgical accessory within the body cavity; and actuating the surgical accessory from outside the body cavity of the patient to interact with a portion of the body cavity.

28. The method of claim 27 wherein the surgical accessory includes a member movable between a rest position and an actuated position, and wherein actuating the surgical accessory comprises moving the movable member toward the actuated position.

29. The method of claim 28 wherein the actuation member is introduced into the cavity separately from the surgical accessory, and wherein the actuation member is detachably coupled with the movable member of the surgical accessory inside the cavity.

30. The method of claim 27 wherein the at least one surgical accessory is introduced into the cavity supported by a surgical accessory support, and is removable from the surgical accessory support within the cavity.

31. The method of claim 30 wherein the surgical accessory support includes a container.

32. The method of claim 27 further comprising decoupling the surgical accessory from the robotic surgical tool inside the cavity.

33. A method of performing minimally invasive robotic surgery in a body cavity of a patient, the method comprising:

introducing at least one surgical accessory into the cavity;

introducing a robotic surgical tool into the cavity;

coupling the surgical accessory with the robotic surgical tool inside the cavity after separately introducing the surgical accessory and the robotic surgical tool into the cavity; and actuating the surgical accessory from outside the cavity of the patient to effect a predetermined treatment, wherein actuating the surgical accessory comprises advancing a clip from a clip storage region to a clip applying region of the surgical accessory and applying the clip to a target region.

34. The method of claim 33 wherein the at least one surgical accessory is introduced into the cavity through a cannula.

35. The method of claim 33 wherein the at least one surgical accessory is introduced into the cavity supported by a surgical accessory support, and is removable from the surgical accessory support within the cavity.

36. The method of claim 35 wherein the surgical accessory support includes a container.

37. A method of performing minimally invasive robotic surgery in a body cavity of a patient, the method comprising:

introducing at feast one surgical accessory into the cavity through a cannula;

introducing a robotic surgical tool into the cavity;

coupling the surgical accessory with the robotic surgical tool inside the cavity after separately introducing the surgical accessory and the robotic surgical tool into the cavity; and actuating the surgical accessory from outside the cavity of the patient to effect a predetermined treatment.

38. The method of claim 37 further comprising decoupling the surgical accessory from the robotic surgical tool inside the cavity.

39. A method of performing minimally invasive robotic surgery in a body cavity of a patient, the method comprising:

introducing at least one surgical accessory into the cavity;

introducing a robotic surgical tool into the cavity;

coupling the surgical accessory with the robotic surgical tool inside the cavity after separately introducing the surgical accessory and the robotic surgical tool into the cavity; and actuating the surgical accessory from outside the cavity of the patient to effect a predetermined treatment, wherein the at least one surgical accessory is introduced into the cavity supported by a surgical accessory support, and is removable from the surgical accessory support within the cavity.

40. The method of claim 39 wherein the surgical accessory includes a member movable between a rest position and an actuated position, and wherein actuating the surgical accessory comprises moving the movable member toward the actuated position.

41. The method of claim 40 wherein the movable member of the surgical accessory is coupled with an actuation member having a proximal portion disposed outside of the cavity of the patient, and wherein actuating the surgical accessory comprises manipulating the actuation member to move the movable member from outside the cavity of the patient.

42. The method of claim 41 wherein the actuation member is introduced into the cavity separately from the surgical accessory, and wherein the actuation member is detachably coupled with the movable member of the surgical accessory inside the cavity.

* * * * *